(12) United States Patent
Uckun et al.

(10) Patent No.: US 6,376,504 B1
(45) Date of Patent: Apr. 23, 2002

(54) PHENETHYL-5-BROMOPYRIDLYTHIOUREA (PBT) AND DIHYDROALKOXYBENZYLOXOPYRIMIDINE (DBABO) DERIVATIVES EXHIBITING SPERMICIDAL ACTIVITY

(75) Inventors: Fatih M. Uckun, White Bear Lake; Osmond D'Cruz, Maplewood, both of MN (US)

(73) Assignee: Parker Hughes Institute, Roseville, MN (US)

( * ) Notice: Subject to any disclaimer, the term of this patent is extended or adjusted under 35 U.S.C. 154(b) by 0 days.

(21) Appl. No.: 09/533,267

(22) Filed: Mar. 20, 2000

Related U.S. Application Data

(62) Division of application No. 09/224,677, filed on Dec. 31, 1998, now Pat. No. 6,136,335.

(51) Int. Cl.$^7$ .................... C07D 239/56; A61K 31/505; A61P 15/06; A61P 31/118

(52) U.S. Cl. ................... 514/274; 544/312; 544/314

(58) Field of Search ............................. 544/312, 314; 514/274

(56) References Cited

U.S. PATENT DOCUMENTS

| | | | |
|---|---|---|---|
| 5,112,835 A | 5/1992 | Miyasaka et al. | 544/302 |
| 5,593,993 A | 1/1997 | Morin, Jr. et al. | 514/247 |
| 5,658,907 A | 8/1997 | Morin, Jr. et al. | 514/247 |
| 5,686,428 A | 11/1997 | Eriksson et al. | 514/50 |
| 5,714,503 A | 2/1998 | Morin, Jr. et al. | 514/332 |
| 5,786,462 A | 7/1998 | Schneider et al. | 536/23.1 |
| 5,998,411 A | * 12/1999 | Vig et al. | 514/235.5 |
| 6,136,335 A | * 10/2000 | Uckun et al. | 514/353 |

FOREIGN PATENT DOCUMENTS

| | | |
|---|---|---|
| EP | 0 420 763 A2 | 4/1991 |
| EP | 0 540 143 A2 | 5/1992 |
| JP | 07025770 | 1/1995 |
| WO | WO 93/03022 | 2/1993 |
| WO | WO 95/06034 | 3/1995 |
| WO | WO 99/47501 | 9/1999 |
| WO | WO 00/03998 | 1/2000 |

OTHER PUBLICATIONS

Ahgren, C., et al., 1995, *Antimicrob. Agents Chemotherapy*, 39, 1329–1335 The PETT Series, a New Class of Potent Nonnucleoside Inhibitors of Human Immunodeficiency Virus Type 1 Reverse Transcriptase.

Baba, M., et al., 1992, *Antiviral Res.*, 17, 245–264 Highly potent and selective inhibition of HIV–1 replication by 6–phenylthiouracil derivatives.

Balzarini, J. et al., 1992, *Proc. Natl. Acad. Sci. U S A*, 89, 4392–4396

2',5'–Bis–O–(tert–butyldimethylsilyl)–3'–spiro–5"–(4"–amino–1", 2"–oxathiole–2",2"–dioxide)pyrimidine(TSAO) nucleoside analogues: Hightly selective inhibitors of human immunodeficiency virus type 1 that are targeted at the viral reverse transcriptase.

Bartlett, P.A. et al., 1989, *Molecular Recognition in Chemical and Biological Problems, Special Pub., Royal Chem. Soc.*, 78, 182–196 Caveat: A Program to Facilitate the Structure–derived Design of Biologically Active Molecules.

Bell, F. W., et al., 1995, *J. Med. Chem.*, 38, 4929–4936 Penethylthaizolethiourea (PETT) Compounds, a New Class of HIV–1 Reverse Transcriptase Inhibitors. 1. Syntheis and Basic Structure–Activity Relationship Studies of PETT Analogs.

Blaney, J.M. and Dixon, J.S., 1993, *Perspectives in Drug Discovery and Design*, 1, 301 A good ligand is hard to find: Automated docking methods.

Bohm, H. J., 1992, *J. Comput. Aided. Mol. Des.*, 6, 593–606 LUDI: rule–based automatic design of new substituents for enzyme inhibitor leads.

Bohm, H.J., 1992, *J. Comp. Aid. Molec. Design*, 6, 61–78 The computer program LUDI: A new mehtod for the de novo design of enzyme inhibitors.

Bohm, H. J.,*J. Comput. Aided. Mol. Des.*, 1994, 8, 243–256; 1996 The development of a simple empirical scoring function to estimate the binding constant for a protein–ligand complex of knwon three–dimensional structure.

Bosworth, N., et al., 1989, *Nature*, 341: 167–168 Scintillation proximity assay.

Brooks, B.R. et al., 1983, *J. Comp. Chem.*, 4, 187–217 CHARMM: A Program for Macromolecular Energy, Minimization, and Dynamics Calculations.

Burkert, U. and Allinger, N.L., 1982, Molecular Mechanics, *ACS Monograph*, 177, 59–78, American Chemical Society, D.C. Methods for the Computation of Molecular Geometry.

Cantrell, A. S., et al., 1996, *J. Med. Chem.*, 39, 4261–4274 Phenethylthiazolythiourea (PETT) Compounds as a New Class of HIV–1 Reverse Transcriptase Inhibitors. 2. Synthesis and Further Structure–Activity Relationship Studies of PETT Analogs.

Chemical substance index page, *Chemical Abstracts, 13th Collective Chemical Substance Index*, Book 52, p. 1272 (1992–1996).

Connolly, M. L., 1983, *Science*, 221, 709–713 Solvent–Accessible Surfaces of Proteins and Nucleic Acids.

(List continued on next page.)

Primary Examiner—Richard L. Raymond
Assistant Examiner—Venkataraman Balasubramanian
(74) Attorney, Agent, or Firm—Merchant & Gould

(57) ABSTRACT

Novel phenethyl-5-bromopyridylthiourea (PBT) and dihydroalkoxybenzyloxopyrimidine (DABO) derivatives exhibiting spermicidal activity as well as anti-viral activity. These novel compounds can be incorporated within contraceptive compositions to provide for spermicidal or sperm-immobilizing activity.

10 Claims, 6 Drawing Sheets

OTHER PUBLICATIONS

D'Cruz, et al., 1996, *Biol. Reprod.*, vol. 54, pp. 1217–1228 Recombinant Soluble Human Complement Receptor Type 1 Inhibits Antisperm Antibody– and Neutrophil–Mediated Injury to Human Sperm.

D'Cruz, et al., 1998, *Biol. Reprod.*, vol. 58, pp. 1515–1526 Spermicidal Activity of Metallocene Complexes Containing Vanadium (IV) in Humans.

Danel, K. et al., 1997, *Acta Chemica Scandinavica*, 51, 426–430 Anti–HIV Active Napthyl Analogues of HEPT and DABO.

Danel, K. et al., 1998, *J. Med. Chem.*, 41, 191–198 Synthesis and Anti–HIV–1 Activity of Novel 2,3–Dihydro–7H–thiazolo[3,2–α]pyrimidin–7–ones.

Danel, K., et al., 1996, *J.Med. Chem.*, 39, 2427–2431 Synthesis and Potent Anti–HIV–1 Activity of Novel 6–Benzyluracil Analogues of 1–[2–Hydroxyethoxy)methyl]–6–(phenylthio)thymine.

Das, K. et al., 1996, *J. Mol. Biol.*, 264, 1085–1100 Crystal Structures of 8–Cl and 9–C1 TIBO Complexed with Wild–type HIV–1 RT and 8–CI TIBO Complexed with the Tyr181Cys HIV–1 RT Drug–resistant Mutant.

Davies et al., 1976, *J. Chem. Society, Perkin Translations 1*, vol. 2, pp. 138–214 Condensed Thiophen Ring Systems. Part XIX. Synthesis of 6,7–Dihydrothieno [3,2–c] pyridines by Intramolecular Cyclistion of 2–(2– or 3–Thienyl)ethyl Isothiocyanate.

De Clercq, E., 1992, *J. Acquired Immune Defic. Syndr. Res. Human. Retrovirus*, 8, 119–134 HIV Inhibitors Targeted at the Reverse Transcriptase.

Ding, J., 1995, et al., *Nat. Struct. Biol.*, 2, 407–415 Structure of HIV–1 RT/TIBO R 86183 complex reveals similarity in the binding of diverse nonnucleoside inhibitors.

Erice, A. et al., 1993, *Antimicrob. Ag. Chemother.*, 37, 835 Anti–Human Immunodeficiency Virus Type 1 Activity of an Anti–CD4 Immunoconjugate Containing Pokeweed Antiviral Protein.

Gittos et al., *J. Chem. Society*, Perkin 1, pp. 169–143 A New Synthesis of Isocyanates.

Goodsell, D.S. and Olson, A.J., 1990, *Proteins: Struct. Funct. Genet.*, 8, 195–202 The Molecular Biology of Human Immunodeficiency Virus Type 1 Infection.

Greene, W. C., 1991, *New England Journal of Medicine*, 324, 308–317 Automated Docking of Substrates to Proteins by Simulated Annealing.

Hira, et al., 1997, *Int. J. STD AIDS*, vol. 8, pp. 243–250 Condom and nonoxynol–9 use and the incidence of HIV infection in serodiscordant couples in Zambia.

Hopkins, A. L. et al., 1996, *J. Med. Chem.*, 39, 1589–1600 Complexes of HIV–1 Reverse Transriptase with Inhibitors of the HEPT Series Reveal Conformational Changes Relevant to the Design of Potent Non–Nucleoside Inhibitors.

Jones, T. A. et al., 1991, *Acta Crystallogr. A.*, 47, 110–119 Improved Methods for Building Protein Models in Electron Denisty Maps and the Location of Errors in these Models.

Kohlstaedt, L. A. et al., 1992, *Science*, 256, 1783–1790 Crystal Structure at 3.5 Å Resolution of HIV–1 Reverse Transcriptase Complexed with an Inhibitor.

Kuntz, I.D., et al., 1995, *J. Mol. Biol.*, 1982, 161, 269–288 A Geometric Approach to Macromolecule–Ligand Interactions.

Larder et al., 1993, *Nature*, 365, 451–453.

Luty, B. A. et al., 1995, *J. Comp. Chem.*, 16, 454–464 A Molecular Mechanics/Grid Methods for Evaluation of Ligand–Receptor Interactions.

Mai, A. et al., 1997, *J. Med. Chem.*, 40, 1447–1454 Dihydro(alkylthio)(napthylmethyl)oxopyrimidines: Novel Non–Nucleoside Reverse Transcriptase Indhibitors of the S–DABO Series.

Marshall, G.R., 1987, *Ann. Ref. Pharmacol. Toxicol.*, 27, 193 Computer–Aided Drug Design.

Martin, Y.C., 1992, *J. Med. Chem.*, 35, 2145–2154 3D Database Searching in Drug Design.

Mao, C. et al., 1998, *Bioorganic & Medicinal Chemistry Letters* 8, pp. 2213–2218 Structure–Based Design of N–[2–(1–Piperidinylethyl)]–N'–[2–(5–Bromopyridyl)]–Thiourea and N–[2–(1–Piperazinylethyl)–N'–[2–(5–Bromopyridyl)]–Thiourea as Potent Non–Nucleoside Inhibitors of HIV–1 Reverse Transcriptase.

Mitsuya, H. et al., 1990, *Science*, 249, 1533–1544 Molecular Targets for AIDS Therapy.

Nishibata, Y. and Itai, A., 1991, *Tetrahedron*, 47, 8985 Automatic Creation of Drug Candidate Structures Based on Receptor Structure. Starting Point for Artificial Lead Generation.

Pauwels, R. et al., 1990, *Nature*, 343, 470–474 Potent and selective inhibitionof HIV–1 replication in vitro by a novel series of TIBO derivatives.

Pontikis, R. et al., 1997, *J. Med. Chem.*, 40, 1845–1854 Synthesis and Anti–HIV Activity of Novel N–1 Side Chain–Modified Analogs of 1–[(2–Hydroxyethoxy)methyl]–6–(phenylthio)thymine (HEPT).

Remington's Pharmaceutical Sciences, Chapter 43, 14th Ed., Mack Publishing Col, Easton PA 18042, USA Topical Drugs.

Ren, J. et al., 1995, *Structure*, 3, 915–926 The structure of HIV–1 reverse transcriptase complexed with 9–chloro–TIBO: lessons for inhibitor design.

Roddy, et al., 1998, *N. Eng. J. Med.*, vol. 339, pp. 504–510 A Controlled Trail of Nonoxynol 9 Film to Reduce Male–To–Female Transmission of Sexually Transmitted Diseases.

Romero, D. L. et al., 1993, *J. Med. Chem.*, 36, 1505–1508 Bis(heteroaryl)piperazine (BHAP) Reverse Transcriptase Inhibitors: Structure–Activity Relationships of Novel Substituted Indole Analogues and the Identification of 1–[(5–Methanesulfonamido–1H–indol–2–yl)–carbonyl]–4–[3–[(1–methylethyl)amino]–pyridinyl]piperazine Monomethanesulfonate (U–90152S), a Second–Generation Clinical Candidate.

Sahlberg, et al., 1998, *Bioorganic & Medicinal Chemistry Letters* 8, pp. 1511–1516 Synthesis and Anti–Hiv Activities of Urea–PETT Analogs Belonging to a New Class of Potent Non–Nucleoside HIV–1 Reverse Transcriptase Inhibitors.

Sudbeck, E. A. et al., 1998, *Antimicrobial Agents and Chemotherapy*, 42(12), 3225–33 Structure–Based Design of Novel Dihydroalkoxybenzyloxopyrimidine Derivatives as Potent Nonnucleoside Inhibitors of the Human Immunodeficiency Virus Reverse Transcriptase.

Tanaka, H. et al., 1991, *J. Med. Chem.*, 34, 349–357 A New Class of HIV–1–Specific 6–Substituted Acyclouridine Derivatives: Synthesis and Anti–HIV–1 Activity of 5– or 6–Substituted Analogues of 1–[(2–Hydroxyethoxy)methyl]–6–(phenylthio)thymine(HEPT).

Tanaka, H. et al., 1994, *Chemical Abstracts*, vol. 120, No. 17, p. 1160 Synthesis of a Potential Photoaffinity Labeling Reagent for HIV–1 Reverse Transcriptase.

Tantillo, C. et al., 1994, *J Mol Biol*, 243, 369–387 Locations of Anti–Aids Drug Binding Sites and Resistance Mutations in the Three–dimensional Structure of HIV–1 Reverse Transcriptase.

Tronchet, JMJ et al., 1997, *Eur. J. Med. Chem.*, vol. 32, pp. 279–299 A QSAR Study Confirming the Heterogeneity of the HEPT Derivatives Series Regarding Their Interaction with HIV Reverse Transcriptase.

Uckun, F. M. et al., 1998, *Antimicrobial Agents and Chemotherapy*, 42, 383 TXU (Anti–CD7)–Pokeweed Antiviral Protein as a Potent Inhibitor of Human Immunodeficiency Virus.

Vig, R. et al., 1998, *Bioorganic & Medicinal Chemistry*, 6:1789–1797 Rational Design and Synthesis of Phenethyl–5–bromopyridyl Thiourea Derivatives as Potent Non–nucleoside Inhibitors of HIV Reverse Transcriptase.

Vig, R. et al., 1998, *Bioorganic & Medicinal Chemistry Letters 8*, pp. 1461–1466 5–Alkyl–2–[(Methylthiomethyl)Thio]–6–(Benzyl)–Pyrimidin–4–(1H)–Ones as Potent Non–Nucleoside Reverse Transcriptase Inhibitors of S–DABO Series.

Weiner, S.J. et al., 1984, *J. Am. Chem. Soc.*, 106, 765–784 A New Force Field For Molecular Mechanical Simulation of Nucleic Acids and Proteins.

Zarling, J. M. et al., 1990, *Nature*, 347, 92–95 Inhibition of HIV replication by pokeweed antiviral protein targeted to $CD4^+$ cells by monoclonal antibodies.

Zhang et al., 1996, *Antiviral Chemistry & Chemotherapy*, 7(5):221–229 Synergistic inhibition of HIV–1 reverse transcriptase and HIV–1 replication by combining trovirdine with AZT, ddI and ddC in vitro.

Uckun et al. Biol. Reprod. 60(6) 1419–1428, 1999. CA 131:111550, 1999.*

D'Cruz, O.J. et al, "Aryl Phosphate Derivatives of Bromo–Methoxy–Azidothymidine Are Dual–Function Spermicides with Potent Anti–Human Immunodeficiency Virus", *Biology of Reproduction*, vol. 59, pp. 503–515 (1998).

D'Cruz, O.J. et al., "Novel Derivatives of phenethyl–5–bromopyridylthiourea and dihydroalkoxybenzyl–oxopyrimidine are dual–function spermicides with potent anti–human immunodeficiency virus activity", *Biol. Reprod.*, vol. 60, No. 6, one page (1999).

* cited by examiner

PHENETHYL-5-BROMOPYRIDLYTHIOUREA (PBT) AND DIHYDROALKOXYBENZYLOXOPYRIMIDINE (DBABO) DERIVATIVES EXHIBITING SPERMICIDAL ACTIVITY

The present application is a divisional application of Ser. No. 09/224,677, filed on Dec. 31, 1998 entitled PHENETHYL-5-BROMOPYRIDYLTHIOUREA (PBT) AND DIHYDROALKOXYBENZYLOXOPYRIMIDINE (DABO) DERIVATIVES EXHIBITING SPERMICIDAL ACTIVITY, now issued as U.S. Pat. No. 6,136,335.

FIELD OF THE INVENTON

The present invention is directed to novel PBT and DABO derivatives. In one particular embodiment, the invention is directed to novel PBT and DABO derivatives that exhibit spermicidal activity.

BACKGROUND OF THE INVENTION

Human immunodeficiency virus (HIV), the etiologic agent of acquired immunodeficiency syndrome (AIDS), is the fastest growing cause of death in women of reproductive age. Heterosexual transmission accounts for 90% of all HIV infections worldwide and constitutes a growing proportion of new HIV infections in the United States. By the year 2000, thirteen million women will be infected with HIV out of a worldwide total of 40 million HIV-infected individuals. In the absence of an effective prophylactic anti-HIV vaccine or antiretroviral therapy, female-controlled vaginal microbicides for curbing mucosal and perinatal HIV transmission are needed.

There is concern that worldwide use of detergent spermicides, such as nonoxynol-9 (N-9) might actually increase the risk of HIV transmission. N-9 has been used for more than 30 years in over-the-counter gels, foams, creams, sponges, films, and foaming tablets designed to kill sperm. Because N-9 has been shown to inactivate HIV in vitro, it is the only topical microbicide currently under consideration for protection against sexually transmitted HIV infection in women. However, the main drawback of using N-9 is its detergent-type effect on epithelial cells. Frequent use of N-9 as a vaginal contraceptive has been associated with an increased risk of cervicovaginal infection, irritation, or ulceration. Since continued use of N-9 can alter the vaginal flora and promote opportunistic infections, it can enhance the susceptibility of the ectocervical epithelium and endocervical mucosa to HIV infection. Furthermore, recent clinical trials have shown that vaginal contraceptives containing N-9 had no effect on the transmission of HIV/AIDS and other STDs when provided as part of an overall prevention program to prevent heterosexual transmission of HIV/AIDS. See, for Example, Roddy et. al., 1998, *N.Eng.J Med.* 339:504–510; Hira et.al., 1997, *Int. J. STD AIDS* 8:243–250)

New, effective, safe, and female-controlled topical microbicides lacking detergent-type membrane toxicity should have clinical advantage over the currently available vaginal microbicides. Physiological fertilization depends on the ability of the ejaculated sperm to swim, bind the zona pellucida, and penetrate the egg. Each of these activities is primarily dependent on sperm motility. Therefore, adding spermicidal function to antiretroviral drugs of choice, such as non-nucleoside inhibitors (NNIs), could be an effective way to curb heterosexual vaginal transmission of HIV as well as prevent conception.

SUMMARY OF THE INVENTION

The present invention provides novel nonnucleoside inhibitors (NNIS) which are phenethyl-5-bromopyridylthiourea (PBT) and dihydroalkoxybenzyloxopyrimidine (DABO) derivatives. These compounds are useful as sperm immobilizing or contraceptive agents. To applicants' knowledge, PBT and DABO derivatives have not previously been studied and recognized as having any contraceptive, e.g., spermicidal, or sperm-inmobilizing, activity.

The invention provides halogenated PBT derivatives having the chemical structure (I), or a pharmaceutically acceptable salt thereof:

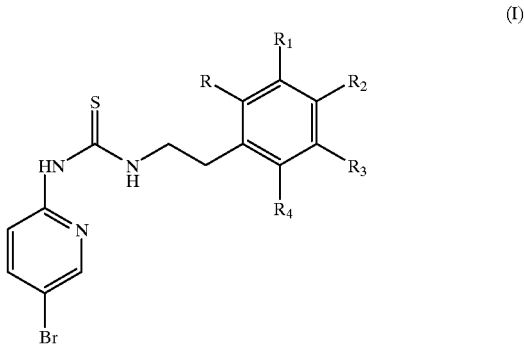

(I)

where R, $R_1$6, $R_2$, $R_3$, and $R_4$ are independently hydrogen, F, Cl, Br, or I, and where at least one of R, $R_1$, $R_2$, $R_3$, and $R_4$ is F, Cl, Br, or I.

The invention also provides a novel DABO derivative compound comprising the formula (III):

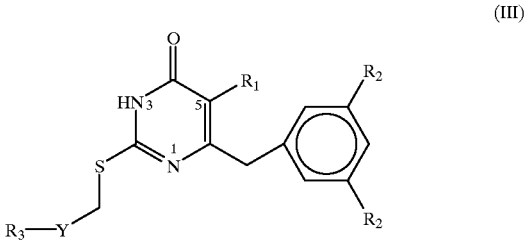

(III)

where $R_1$ and $R_2$ are alike or different, and are hydrogen, halo, alkyl, alkenyl, hydroxy, alkoxy, thioalkyl, thiol, phosphino, ROH, or RNH group, where R is alkyl; Y is S or O; and $R_3$ is alkyl, alkenyl, aryl, aralkyl, ROH, or $RNH_2$ group, where R is alkyl; or a pharmaceutically acceptable salt thereof.

The invention additionally provides a method of inhibiting conception in a mammal. The method comprises contacting mammalian sperm with an effective spermicidal amount of a novel halogenated PBT derivative or a novel DABO derivative of the invention.

Another aspect of the invention is a method for inhibiting the motility of sperm. The method comprises contacting sperm with a sperm mobility-inhibiting effective amount of a halogenated PBT derivative or a DABO derivative of the invention.

The invention also provides a composition comprising an effective spermicidal amount of a spermicidal agent, and a pharmaceutically acceptable carrier, diluent, or vehicle. The spermicidal agent comprises a halogenated PBT derivative or a DABO derivative of the invention.

The invention also provides a spermicidal article comprising a halogenated PBT derivative or a DABO derivative of the invention.

Other aspects of the invention will become apparent to those skilled in the art upon review of the following drawings, detailed description, examples and claims.

BRIEF DESCRIPTION OF THE DRAWINGS

FIG. 5B shows sperm exposed to 0.5% DMSO alone; FIG. 5C shows sperm exposed to 500 $\mu$M F-PBT; and FIG. 5D shows sperm exposed to 500 $\mu$M S-DABO. None of the FIGS. 5B, 5C, or 5D show increased acrosome reaction of the sperm at 6 hours of incubation. FIG. 5E shows sperm exposed to 500 $\mu$M of N-9, and shows only acrosome-reacted sperm. (original magnification× 1000).

DETAILED DESCRIPTION

Definitions

Figure 1:
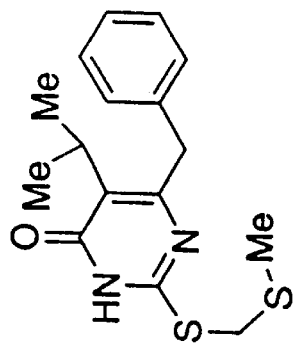
FIG. 1 shows the chemical structures of: N-[2-(2,5-dimethoxyphenethyl)]-N'-[2-(5-bromopyridyl)]thiourea (D-PBT); N-[2-(2-fluorophenethyl)]-N'-[2-(5-bromopyridyl)]-thiourea (F-PBT); 5-isopropyl-2-[(methylthiomethyl)thio]- 6-(benzyl)-pyrimidin-4-(1H)-one (S-DABO); and N-[2-(2-pyridyl)ethyl]-N'-[2-bromopyridyl)]-thiourea (trovirdine, a PETT derivative).
Figure 1:
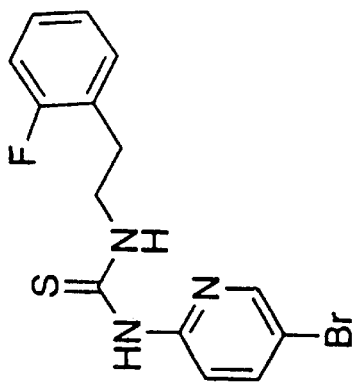
Figure 1:
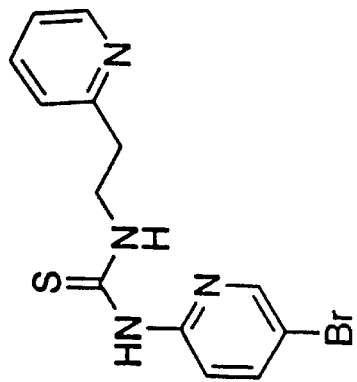
Figure 1:
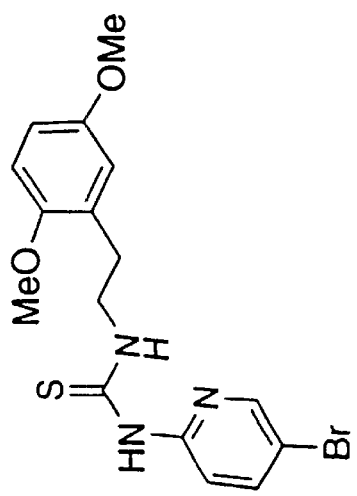

All scientific and technical terms used in this application have meanings commonly used in the art unless otherwise specified. As used in this application, the following words or phrases have the meanings specified.

As used herem, "DABO" means the compound dihydroalkoxybenzyloxopyrimidine.

As used herein, "S-DABO" means the compound 5-isopropyl-2-[(methylthiomethyl)thio]-6-(benzyl)-pyrimdin-4-(1H)-ones.

As used herein, "PBT" means the compound phenethyl-5-bromopyridylthiourea.

As used herein, "F-PBT" means the compound N-[2-(2-fluorophenethyl)]-N'-[2-(5-bromopyridyl)]-thiourea.

As used herein, "D-PBT" means the compound N-[2-(2, 5-dimethoxyphenethyl)]-N'-[2-(5-bromopyridyl)]-thiourea.

As used herein, "N-9" means the virucidal/spermicide, nonoxynol-9.

As used herein, "reverse transcriptase (RT)" refers to an enzyme having an NNI binding site similar to that of HIV-1 RT.

As used herein, a "nonnucleoside inhibitor (NNI)" of HIV reverse-transcriptase (HIV-RT) means a compound which binds to an allosteric site of HIV-RT, leading to noncompetitive inhibition of HIV-RT activity. Examples of nonnucleoside inhibitors of HIV-RT include, but are not limited to, S-DABO, F-PBT, and D-PBT.

As used herein, the terms "analog" or "derivative" are used interchangeably to mean a chemical substance that is related structurally and functionally to another substance. An analog or derivative contains a modified structure from the other substance, and maintains the function of the other substance, in this instance, maintaining the ability to interact with an NNI-RT binding site. The analog or derivative need not be, but can be synthesized from the other substance. For example, a DABO analog or derivative means a compound structurally related to DABO, but not necessarily made from DABO.

As used herein, "pharmaceutically acceptable salt" refers to a salt that retains the desired biological activity of the parent compound and does not impart any undesired toxicological effects. Examples of such salts include, but are not limited to, (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, firrnaric acid, gluconic acid, citric acid, malic acid, ascorbic acid, benzoic acid, tannic acid, pamoic acid, alginic acid, polyglutamic acid, naphthalenesulfonic acids, naphthalenedisulfonic acids, polygalacturonic acid; (b) salts with polyvalent metal cations such as zinc, calcium, bismuth, barium, magnesium, aluminum, copper, cobalt, nickel, cadmium, and the like; or (c) salts formed with an organic cation formed from N,N'-dibenzylethylenediamine or ethylenediamine; or (d) combinations of (a) and (b) or (c), e.g., a zinc tannate salt; and the like. The preferred acid addition salts are the trifluoroacetate salt and the acetate salt.

As used herein, "pharmaceutically acceptable carrier" includes any material which, when combined with a compound of the invention, allows the compound to retain biological activity, such as the ability to inhibit sperm activity, and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline. Compositions comprising such carriers are formulated by well known conventional methods (see, for example, Remington's Pharmaceutical Sciences, Chapter 43, 14th Ed., Mack Publishing Col, Easton Pa. 18042, USA).

Compounds

In the course of pursuing agents having improved activity against HIV, novel NNIs of HIV-1 reverse transcriptase (RT) were synthesized. U.S. patent application Ser. No. 09/040,538, filed on Mar. 17, 1998, which is herein incorporated by reference for all purposes, discloses nonnucleoside inhibitors of reverse transcriptase, an NNI composite binding pocket of HIV-RT, and methods for use thereof.

It was unexpectedly discovered that certain of these NNIs possess spemicidal and/or sperm-immobilizing activity, making them useful as active agents for contraceptive and sperm immobilization products and methods. NNIs possessing the spemicidal activity include novel derivativesof PBT and DABO. The derivatives of PBT and DABO of the invention are particularly useful in forming contraceptive products that can reduce the spread of sexually transmitted diseases, specifically the spread of HIV. Contacting sperm with these spermicidal NNIs inhibits the motility of the sperm and has the desired spermicidal and/or conception-inhibiting functions.

PBT derivatives exhibiting significant spermicidal activity include halogen substituted PBT derivatives having the chemical structure (I) shown below, or a pharmaceutically acceptable salt thereof:

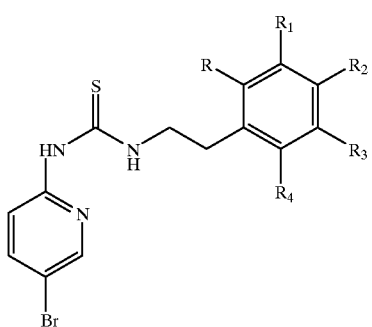

(I)

where R, $R_1$, $R_2$, $R_3$, and $R_4$ are independently hydrogen, F, Cl, Br, and I, and wherein at least one of R, $R_1$, $R_2$, $R_3$, and $R_4$ is F, Cl, Br, or I.

Preferably, one of R, $R_1$, $R_2$, $R_3$, and $R_4$ in structure (I) is F or Cl. Some, but not all of the suitable halogen-substituted PBT derivatives of the invention are listed below:

N-[2-(2-fluorophenethyl)]-N'-[2-(5-bromopyridyl)]-thiourea

N-[2-(2-chlorophenethyl)]-N'-[2-(5-bromopyridyl)]-thiourea

N-[2-(3-fluorophenethyl)]-N'-[2-(5-bromopyridyl)]-thiourea

N-[2-(3-chlorophenethyl)]-N'-[2-(5-bromopyridyl)]-thiourea

N-[2-(4-fluorophenethyl)]-N'-[2-(5-bromopyridyl)]-thiourea

N-[2-(4-chlorophenethyl)]-N'-[2-(5-bromopyridyl)]-thiourea

One of the more preferred PBT derivatives of the invention is N-[2-(2-fluorophenethyl)]-N'-[2-(5-bromopyridyl)]-thiourea (F-PBT) which has the chemical structure (II) shown below:

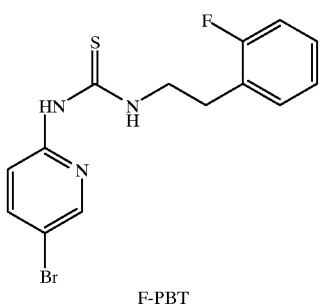

(II)

F-PBT

PBT derivatives of the invention can be synthesized as described in the Examples herein, and as described in Vig et al., BIOORG. MED. CHEM., 6:1789–1797 (1998). In brief, 2-amino-5-bromopyridine is condensed with 1,1-thiocarbonyl diimidazole to furnish the precursor thiocarbonyl derivative. Further reaction with appropriately halogen-substituted phenylethylamine gives the target halogenated PBT derivatives.

DABO derivatives exhibiting significant spermicidal activity include DABO derivatives having the chemical structure (III) shown below, or a pharmaceutically acceptable salt thereof:

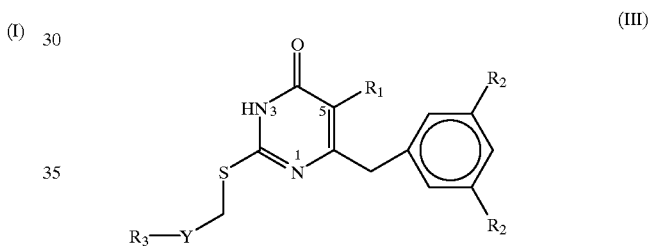

(III)

where $R_1$ and $R_2$ are alike or different, and are hydrogen, halo, alkyl, alkenyl, hydroxy, alkoxy, thioalkyl, thiol, phosphino, ROH, or RNH group, where R is alkyl. Preferably, one or more of $R_1$ and $R_2$ is an alkyl having 1 to 3 carbonatones, ($C_1$–$C_3$), such as methyl (Me), ethyl (Et), or isopropyl (i-Pr). Preferably, $R_1$ is alkyl, alkenyl, ROH, or $RNH_2$. $R_2$ is preferably halo, alkyl, or $C_1$–$C_3$ alkoxy;

Y is S or O, and is preferably S. $R_3$ is alkyl, alkenyl, aryl, aralkyl, ROH, or RNH group, where R is alkyl, and is preferably $C_1$–$C_3$ alkyl.

Preferred DABO derivatives include compounds having the chemical structure (IV) shown below, or a pharmaceutically acceptable salt thereof:

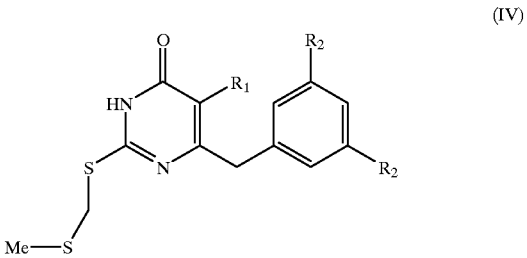

(IV)

where $R_1$ is Me, Et, or i-Pr and $R_2$ is H or Me.

Some, but not all, of the suitable DABO derivative compounds of the invention include compounds (a) through (d) listed below, or a pharmaceutically acceptable salt thereof:

(a) 5-methyl-2-[(methylthiomethyl)thio]-6-benzyl-pyrimidin-4-1H-one, (b) 5-ethyl-2-[(methylthiomethyl)thio]-6-benzyl-pyrimidin-4-1H-one, (c) 5-isopropyl-2-[(methylthiomethyl)thio]-6-benzyl-pyrimidin-4-1H-one, and (d) 5-isopropyl-2-[(methylthiomethyl)thio]-6-(3,5-dimethylbenzyl)-pyrimidin-4-1H-one.

One of the more preferred DABO derivatives of the invention is the compound 5-isopropyl-2-[(methylthiomethyl)thio]-6-(benzyl)-pyrimidin-4-(1H)-ones (S-DABO), and pharmaceutically acceptable salts thereof, which is exemplified by the chemical structure (V) shown below:

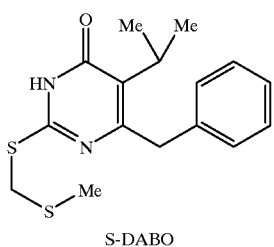

S-DABO (V)

DABO derivatives can be prepared as described in the Examples herein, and as described in Vig et al., BIOORG MED CHEM LETTERS, 8:1461–1466 (1998).

The general synthesis scheme for the preparation of DABO derivatives (a) through (d) listed above is as follows:

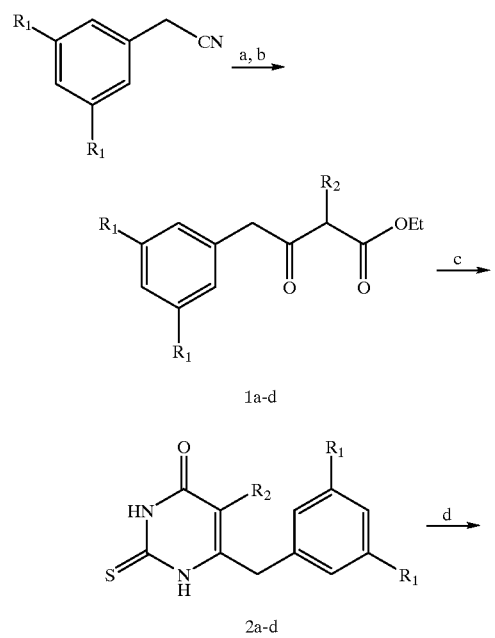

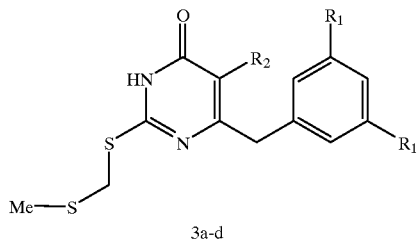

| 1–3 | $R_1$ | $R_2$ |
|---|---|---|
| a | H | Me |
| b | H | Et |
| c | H | i-Pr |
| d | Me | i-Pr |

Reagents and conditions) $R_2$CHBrCOOEt/Zn/THF, b) HCl(aq), c) $(H_2N)_2$CS/Na/EtOH, d) DMF, $K_2CO_3$, Chloromethyl methyl sulfide, 15 h.

Briefly, ethyl-2-alkyl-4-(phenyl)-3-oxobutyrates 1a–d were obtained from commercially available phenyl acetonitrile. The β-ketoesters were condensed with thiourea in the presence of sodium ethoxide to flrnsh the corresponding thiouracils 2a–d. Compounds (1a–d and 2a–d) were produced by a methods previously described (Danel, K. et al., Acta Chemica Scandinavica, 1997, 51, 426–430; Mai, A. et al., J. Med. Chem., 1997, 40, 1447–1454; Danel, K. et al., J. Med. Chem., 1998, 41, 191–198).

Subsequent reaction of thiouracil with methyichioromethyl sulfide in N,N-dimethylformamide (DMF) in the presence of potassium carbonate afforded compounds 3a–d in moderate yields. A mixture of thiouracil compound 2 (1 mmol), methylchloromethyl sulfide (1 mmol), and potassium carbonate (1 mmol) in anhydrous DMF (5 ml) was stirred overnight at room temperature. After treatment with water (50 ml), the solution was extracted with ethyl acetate (3×50 ml). The combined extracts were washed with saturated NaCl (2×50 ml), dried (MgSO$_4$), filtered and concentrated in vacuo to give the crude products 3a–d which were purified by column chromatography (hexane: ethyl acetate eluent).

The purity and physicochemical properties of some PBT derivatives and DABO derivatives are described in the Examples herein, and were reported in detail in Vig et al., BIOORG. MED. CHEM., 6:1789–1797 (1998); and in Vig et al., BIOORG MED CHEM LETTERS, 8:1461–1466 (1998).

Compositions, Articles and Methods

PBT and DABO derivatives of the present invention can be formulated into compositions for spermicidal use. Such compositions are intended particularly for use in mammals, i.e. any class of higher vertebrates that nourish their young with milk secreted from mammary glands, for example humans, rabbits and monkeys. It is also contemplated that the compositions may be used as sperm immobilization compositions. It is expected that the present invention will be used by humans in most practical applications.

The compositions of the present invention contain one or more spermicidal PBT and DABO derivatives, and pharmaceutically acceptable salts thereof, as disclosed above. The amount of spermicidal PBT and DABO derivatives employed generally will be that amount necessary to achieve the desired spermicidal and anti-viral protective results. The amounts can be varied as needed for specific compositions. The amount of spermicidal PBT and DABO derivatives will typically range from about 0.025 to 0.5 weight percent based on the total weight of the contraceptive composition. Preferably, the amount of the spermicidal PBT and DABO derivatives employed will be from about 0.05 to 0.5 weight percent, and more preferably from about 0.05 to 0.25 weight percent, based on the total weight of the composition.

The compositions of the present invention may contain not only the spermicidal PBT and DABO derivatives, but also pharmaceutically acceptable carriers, diluents or vehicles as needed, i.e., materials for appropriately delivering and/or maintaining the spermicidal NNIs to a site for contact with sperm and so as to provide the desired spermicidal and/or anti-viral protective activity.

One advantageous component in the pharmaceutical composition for administration of a spermicide is a polymeric delivery component as described in U.S. Pat. No. 5,595,980, which patent is incorporated herein by reference. It has been found that such polymeric delivery component enhances the effectiveness of a spermicide and reduces vaginal irritation on administration.

In addition to the polymeric component, the balance of the contraceptive compositions, i.e., typically from about 0.1 to 99.8% and often about 50 to 99.8 weight percent, may optionally comprise one or more cosmetic ingredients. Such cosmetic ingredients are known to those skilled in the art and are often referred to in the art as diluents, solvents and adjuvants. Typically cosmetic ingredients include, for example; water, ethyl alcohol, isopropyl alcohol, glycerin, glycerol propylene glycol, sorbitol and other high molecular weight alcohols. In addition, contraceptive compositions may contain minor amounts, e.g. from about 0.1 to 5% weight based on the weight of the contraceptive compositions, of other additives, such as, for example; stabilizers, surfactants, menthol, eucalyptus oil, other essential oils, fragrances, and the like. Polyoxyethylene 20 sorbitan monolaurate is a preferred stabilizer for use in the compositions. The selection and amounts of cosmetic ingredients, other additives, and blending procedures can be carried out in accordance with techniques well-known in the art.

The spermicidal active ingredients, and contraceptive compositions containing the same, of the present invention may be delivered to the vagina of a mammal by any means known to those skilled in the art. Typical forms for delivery of the compositions include, for example; creams, lotions, gels, foams, intervaginal devices such as sponges, condoms, including female condoms, suppositories, and films. In addition, the contraceptive compounds and compositions of the present invention may be used as personal care products, such as, for example, condom lubricants, and the like. Such lubricants may comprise commonly known ingredients such as, for example: humectants; e.g., glycerin, sorbitol, mannitol, glycols and glycol ethers; buffers, e.g., glucono-d-lactone; germicides or bactericides; e.g., chlorhexidine gluconate; preservatives, e.g., methylparaben; viscosifiers; e.g., hydroxyethyl cellulose, etc.; other adjuvants; e.g., colors and fragrances; in addition to the compositions of the present invention. Those skilled in the art will recognize that the physical properties, e.g., viscosity, of such delivery forms may vary widely. For example, the viscosity of a gel form of the composition of the present invention, e.g., 150,000 centipoise, may be substantially higher than the viscosity of lotion form of the composition of the present invention, e.g., 100 centipoise. Further details concerning the materials, ingredients, proportions and procedures of such delivery forms can be selected in accordance with techniques well-known in the art.

The contraceptive compositions of the present invention are preferably administered to a site for contacting sperm, such as to the vagina of a mammal, in a dosage which is effective to immobilize sperm, e.g. sperm present in the vagina, and/or to inhibit sperm penetration of cervical mucus. Typical dosages range between about 0.0001 to 0.001 grains of the composition per kilogram of body weight of the mammal.

Intervaginal devices also may be used to aid in the administration of the spermicidal active ingredients or contraceptive compositions containing the same as described in U.S. Pat. No. 5,069,906, the disclosure of which is incorporated herein by reference.

In administering the spermical active ingredients in the form of the above compositions, the compositions also may be formulated to release the spermicide both rapidly and/or with a prolonged release of the drug. Such a formulation providing both rapid and prolonged release has been described in U.S. Pat. No. 4,707,362, which also is incorporated herein by reference.

It is also contemplated that the spermicidal NNIs of the invention may be incorporated into a spermicidal article such as a vaginal insert, a condom, or other such device, such that when the article is used, the spermicidal NNI may be delivered to contact sperm.

The invention will be explained further with reference to the following examples, which should not be considered to limit the invention.

EXAMPLES

In an effort to develop a vaginal microbicidal contraceptive potentially capable of preventing HIV transmission as well as providing fertility control, novel non-nucleoside inhibitors (NNIs) of HIV-1 reverse transcriptase (RT) were synthesized and examined for dual-function anti-HIV and spermicidal activity.

The synthesis of novel NNIs as inhibitors of HIV RT was based on a computer model in which a composite binding pocket was constructed from 9 individual crystal structures of RT-NNI complexes. [INERT CITATION] The novel NNIs include: N-[2-(2,5-dimethoxyphenethyl)]-N'-[2-(5-bromopyridyl)]-thiourea (D-PBT), N-[2-(2-fluorophenethyl)]-N'-[2-(5-bromopyridyl)]-thiourea (F-PBT), and 5-isopropyl-2-[(methylthiomethyl)thio]-6-(benzyl)-pyrimidin-4-(1H)-one (S-DABO).

As seen in FIG. 1, the NNI trovirdine could be viewed as two chemical groups linked together by a thiourea group. One half of the molecule is composed of a pyridylthiourea moiety which forms an intramolecular hydrogen-bonded heterocyclic ring. The other half of the molecule is a pyridyl ring separated from the thiocarbonyl group by an ethyl linker. Computer docking procedures using trovirdine revealed multiple sites which could be used for the incorporation of larger finctional groups surrounding the pyridyl ring, the ethyl linker, and near the 5-bromo position of trovirdine. Therefore, strategically designed-functional groups were added to yield new derivatives with potentially higher affinity for the NNI binding pocket of HIV RT. Two new PBT derivatives (D-PBT and F-PBT) were synthesized by replacing the 2-pyridyl ring of trovirdine with 2,5 dimethoxyphenyl moiety (D-PBT) or a fluorine atom at the ortho position (F-DBT). Derivatization of DABO was achieved by modeling studies of potent HEPT derivatives and by the addition of a isopropyl group at the C-5 position of the thymine ring (S-DABO).

The anti-HIV activity of these three novel NNIs (D-PBT, F-DBT and S-DABO) was compared with that of trovirdine and of the virucidal/spermicide, nonoxynol-9 (N-9), by measuring viral RT activity and p24 antigen production as markers of viral replication using HIV-infected human peripheral blood mononuclear cells (PBMCs). The effects on sperm motion kinematics and sperm membrane integrity were analyzed by computer-assisted sperm analysis (CASA) and by confocal laser scanning microscopy (CLSM), respectively. The growth-inhibitory effects of NNI versus N-9 against normal human ectocervical and endocervical epithelial cells were tested using the MTT assay. All three NNIs were potent inhibitors of purified recombinant HIV RT and abrogated HIV replication in PBMCs at nanomolar concentrations ($IC_{50}$<1 nM) when compared with N-9 or trovirdine [$IC_{50}$ values of 2.2 μM and 0.007 μM respectively]. Two NNIs, F-PBT and S-DABO, also exhibited concentration- and time-dependent spermicidal activity.

I. MATERIALS AND METHODS

A. Chemical Synthesis

All chemicals were used as received from Aldrich Chemical Company (Milwaukee, Wis.). All reactions were carried out under nitrogen. Column chromatography was performed using EM Science silica gel 60 and one of the following solvents: ethyl acetate, methanol, chloroform, hexane, or methylene chloride. Nuclear magnetic resonance (NMR) spectra were recorded on a Varian (Palo Alto, Calif.) 300 MHz instrument (Mercury 2000 model) and chemical shifts (δ) are reported in parts per million (ppm) relative to tetramethylsilane as an internal standard at 0 ppm. $^{13}$C NMR spectra were recorded at 75 MHz in $CDCl_3$ on the same instrument using a proton decoupling technique. The chemical shifts reported for $^{13}$C NMR are referenced to the chloroform triplet at 77 ppm. Melting points were measured using a Mel-Temp 3.0 (Laboratory Devices Inc., Holliston, Mass.) melting apparatus and are uncorrected. UV spectra were recorded from a Beckmann (Fullerton, Calif.) model DU 7400 U/V is spectrometer using a cell path length of 1 cm and methanol solvent. Fourier Transform Infrared spectra were recorded using an FT-Nicolet (Madison, Wis.) model Protege 460 instrument. Mass spectrum analysis was performed using a Hewlett-Packard (Palo Alto, Calif.) Matrix Assisted Laser Description timeof-flight (MALDI-TOF) spectrometer (model G2025A) in the molecular ion detection mode (matrix used was cyanohydroxycinnamic acid). Some samples were analyzed using a Finnigan (Madison, Wis.) MAT 95 instrument. Elemental analysis was performed by Atlantic Microlabs (Norcross, Ga.).

1. Chemical Synthesis of Trovirdine

Trovirdine, (N-[2-(2-pyridyl)ethyl]-N'-[2-bromopyridyl]-thiourea), was synthesized according to literature procedure. See, Cantrell et al., *J MED CHEM* 39:4261–4274 (1996).

2. Chemical Synthesis of D-PBT

Compound D-PBT ([N-[2-(2,5-dimethoxyphenethyl)]-N'-[2-(5-bromopyridyl)]thiourea) was synthesized as described in Vig et al., *BIOORG. MED. CHEM.*, 6:1789–1797 (1998).

In brief, D-PBT was synthesized as described in Scheme 1.

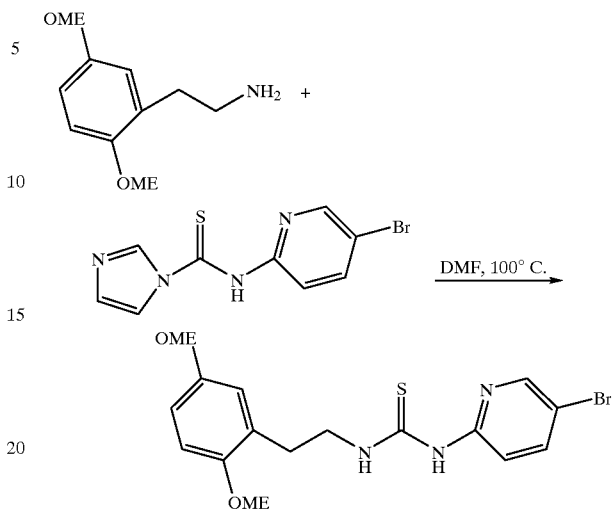

Scheme 1

The purity and properties of the resultant D-PBT were as follows: white solid (2 g, 67%); mp 133–138° C.; UV (MeOH) λmax: 202, 205, 231, 276 and 300 nm; IR(KBr Disc) ν 3209, 3152, 3078, 3028, 2951, 2831, 1595, 1533, 1468, 1306, 1227, 1095, 1059, 1022, 862, 825, 796, 707 $cm^{-1}$; $^1$H NMR($CDCl_3$) δ 11.24 (br s, 1H), 9.30 (br s, 1H), 8.10–8.09 (d, 1H), 7.65 (dd, 1H), 6.82–6.76 (m, 4H), 4.03–3.97 (q, 2H), 3.77 (s, 3H), 3.76 (s, 3H), 3.00–2.96 (t, 2H); $^{13}$C NMR($CDCl_3$) δ 178.7, 153.1, 151.8, 151.7, 146.5, 140.9, 128.1, 117.7, 113.3, 112.6, 111.2, 110.9, 55.7, 55.5, 45.6, and 29.9; MALDI-TOF mass found, 394.0 (M−1), 396.0 (M+1), calculated, 395.0; Anal. ($C_{16}H_{18}BrN_3O_2S$) C, H, N, S, Br.

3. Chemical Synthesis of F-PBT

Compound F-PBT (N-[2-(2-fluorophenethyl)]-N'-[2-(5-bromopyridyl)]-thiourea) was synthesized as described in Vig et al., *BIOORG. MED. CHEM.*, 6:1789–1797 (1998).

More specifically, F-PBT was synthesized according to Scheme 2. In brief, 2-amino-5-bromopyridine was condensed with 1,1-thiocarbonyl diimidazole to furnish the precursor thiocarbonyl derivative. Further reaction with appropriately substituted phenylethyl amine, in this case 2-flourophenethyl amine, gave the target F-PBT.

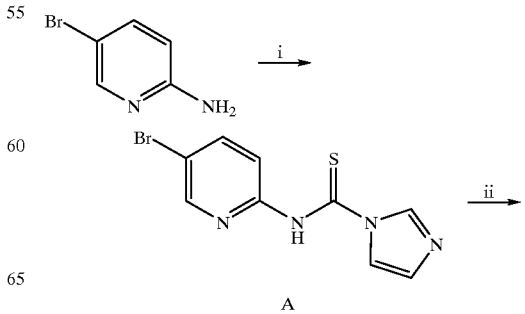

Scheme 2

-continued

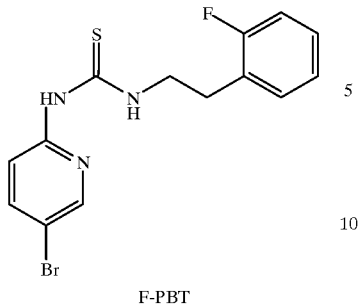

F-PBT

-continued

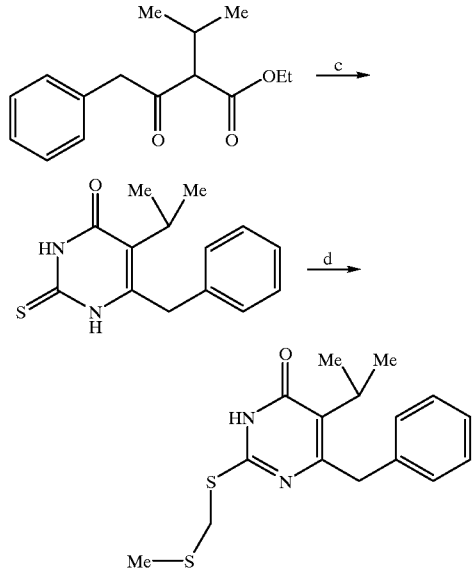

where: i) 1,1-thiocarbonyldiimidazole, acetonitrile, room temperature, 12 hours; and ii) DMF, 2-flourophenethyl amine, 100° C., 15 hours.

The following procedures were specifically used for the synthesis of F-PBT: Thiocarbonyldiimidazole (8.90 g, 50 mmol) and 2-amnino-5-bromo pyridine (8.92 g, 50 mmol) were added to 50 mL of dry acetonitrile at room temperature. The reaction mixture was stirred for 12 hours and the precipitate filtered, washed with cold acetonitrile (2×25 mL), and dried under vacuum to afford 11.40 g (80%) of compound A. To a suspension of compound A (0.55 eqv) in dimethyl formamide (15 mL) an appropriate amine, in this case 2-flourophenethyl amine, (0.50 eqv) was added. The reaction mixture was heated to 100° C. and stirred for 15 hours. The reaction mixture was poured into ice-cold water and the suspension was stirred for 30 minutes. The product was filtered, washed with water, dried, and further purified by column chromatography to furnish the target compounds in good yields.

The purity and properties of the resultant N-[2-(2-fluorophenethyl)]-N'-[2-(5-bromopyridyl)]-thiourea (F-PBT), were as follows: yield: 71%; mp 156–157° C.; UV (MeOH) λmax: 209, 256, 274 and 305 nm; IR(KBr) ν 3446, 3234, 3163, 3055, 2935, 1672, 1595, 1560, 1531, 1466, 1390, 1362, 1311, 1265, 1227, 1169, 1136, 1089, 1003, 864, 825, 756 cm$^{-1}$; $^1$H NMR (CDCl$_3$) δ 11.36 (br s, 1H), 9.47 (br s, 1H), 8.05–8.04 (d, 1H), 7.72–7.68(dd, IH), 7.30–7.03 (m, 4H), 6.87–6.84 (d, 1H), 4.06–3.99 (q, 2H), 3.10–3.05 (t, 2H); $^{13}$C NMR(CDCl$_3$) δ 179.1, 163.1, 151.7, 146.2, 141.1, 131.2, 131.1, 128.5, 128.4, 124.1, 115.5, 115.2, 113.6, 112.2, 45.8 and 28.2; $^{19}$F NMR(CDCl$_3$) δ −42.58 & −42.55 (d); Maldi Tof found: 355.0 (M+1), calculated: 354.0; Anal. ($C_{14}H_{13}BrFN_3S$) C, H, N, S.

4. Chemical Synthesis of S-DABO

S-DABO, 5-isopropyl-2-[(methylthiomethyl)thio]-6-(benzyl)-pyrimidin-4-(1H)-one (S-DABO) was prepared as described in Vig et al., *BIOORG MED CHEM LETTERS*, 8:1461–1466 (1998).

More specifically, S-DABO was prepared as shown in Scheme 3.

Scheme 3

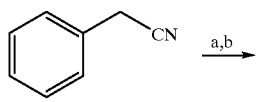

where: a) $R_2$CHBrCOOEt/Zn/THF,
b) HCl(aq),
c) $(H_2N)_2$CS/Na/EtOH,
d) DMF, $K_2CO_3$, Chloromethyl methyl sulfide, 15 hours.

In brief, ethyl-2-isopropyl-4-(phenyl)-3-oxobutyrate was obtained from commercially available phenylacetonitrile. The β-ketoester was condensed with thiourea in the presence of sodium ethoxide to furnish the thiouracil. The ethyl-2-isopropyl- 4-(phenyl)-3-oxobutyrate and the thiouracil compounds were produced by methods previously described (Danel, K. et al., *Acta Chemica Scandinavica*, 1997, 51, 426–430; Mai, A. et al., *J. Med. Chem.*, 1997, 40, 1447–1454; Danel, K. et al., *J. Med. Chem.*, 1998, 41, 191–198). Subsequent reaction of thiouracil with methytchloromethyl sulfide in N,N-dimethylformamide (DMF) in the presence of potassium carbonate afforded compounds 3a–d in moderate yields A mixture of thiouracil compound 2 (1 mmol), methylchloromethyl sulfide (1 mmol), and potassium carbonate (1 mmol) in anhydrous DMF (5 ml) was stirred overnight at room temperature. After treatment with water (50 ml), the solution was extracted with ethyl acetate (3×50 ml). The combined extracts were washed with saturated NaCl (2×50 ml), dried (MgSO$_4$), filtered and concentrated in vacuo to give the crude products 3a–d which were purified by column chromatography on silica gel 60 using hexane/ethyl acetate as the eluent.

The purity and properties of the resultant 5-isopropyl-2-[(methylthiomethyl)thio]-6-benzyl-pyrimidin-4-1H-one (S-DABO) were as follows: Yield 57%; mp 116–117° C.; $^1$H NMR(CDCl$_3$): δ 1.22 (d, 6H), 2.07 (s, 3H), 3.03 (q, 1H), 3.88 (s, 2H), 4.21 (s, 2H), 7.24–7.13 (m, 5H), 12.43 (s, 1H); $^{13}$C NMR(CDCl$_3$): δ 15.4 (SCH$_3$), 19.6 (CH$_3$), 28.0 (CH), 36.3 (CH$_2$Ph), 40.9 (SCH$_2$), 125.3 (C-5), 138.3–126.3 (Ph), 155.5 (C-6), 161.1 (C-4), 164.5 (C-2); Cl-MS 321.1 (M+1).

B. In Vitro Assays of Anti-HIV Activity

The HTLV$_{IIIB}$ strain of HIV-1 was propagated in CCRF-CEM cells and the virus stocks obtained from cell-free supernatants of infected cells were titered using MT-2 cells. Cell-free supernatants were harvested and frozen in 1 ml aliquots at −70° C. Titration of the stock virus was performed using MT-2 cells and the cytopathic effect of the virus used in this study was typical of HIV-1 on MT-2 cells.

For in vitro assays of the anti-HIV-1 activities of the test drugs, D-PBT, F-PBT, S-DABO, trovirdine, and N-9 (IGEPAL CO-630; Rhone Poulenc, Cranbury, N.J.), normal peripheral blood mononuclear cells (PBMCs) from HIV-1 negative donors were cultured for 72 hours in RPMI 1640 medium (Gibco-BRL, Grand Island, N.Y.) with 20% (v/v) heat-inactivated fetal calf serum, 3% interleukin-2, 2 mM L-glutamine, 25 mM HEPES, 2 g/L $NaHCO_3$, 50 µg/ml gentamicin, and 4 µg/ml phytohemagglutinin prior to exposure to HIV-1 at a multiplicity of infection of 0.1 during a 1-hour adsorption period at 37° C. in a humidified 5% $CO_2$ atmosphere. Stock solutions (10 mM) of NNIs, trovirdine, D-PBT, F-PBT, and S-DABO were prepared in dimethylsulfoxide (DMSO) and N-9 was diluted in culture medium. Cells were cultured for 7 days in 96-well microtiter plates (100 µl/well; $2 \times 10^6$ cells/ml, triplicate wells) in the presence and absence of various concentrations (0.001 µM to 100 µM) of the anti-HIV agents. Cells from non-infected controls were handled in the same way except the virus was omitted from the preparation. Aliquots of culture supernatants were removed from the wells on the 7th day after infection for RT assays and p24 antigen, as previously described in the following references: Erice et al., ANTIMICROB AG CHEMOTHER, 37:835–838 (1993); Uckun et al., ANTIMICROB AGENTS CHEMOTHER, 42:383–388 (1998); and Zarling et al., Nature 347:92–95 (1990).

The p24 enzyme immunoassay was the unmodified kinetic assay available commercially (Coulter Corporation/ Immunotech, Inc., Westbrook, Me.). The assay uses a murine monoclonal antibody to the HIV core protein coated onto microwell strips to which the antigen present in the test culture supernatant sample binds. Id. The plates were read on a ELISA reader (Molecular Devices, Sunnyvale, Calif.) at 650 nm and p24 levels, expressed as ng/ml, were calculated against known standards supplied by Coulter/ Immunotech, Inc. Percent viral inhibition was calculated by comparing the p24 values for the test substance-treated infected cells with the p24 values for untreated infected cells (i.e., virus controls).

Compounds, D-PBT, F-PBT, S-DABO, and trovirdine were tested for RT inhibitory activity against purified recombinant HIV RT using the cell-free Quan-T-RT system (Amersham Corp., Arlington Heights, Ill.), which utilizes the scintillation proximity assay principle. See, Bosworth N, and Towers P, Scintillation proximity assay, NATURE, 341:167–168 (1989). In the assay, a DNA/RNA primer/ template is bound to SPA beads via a biotin/streptavidin linkage. The primer DNA is a 16-mer oligo(T) which has been annealed to a poly(rA) template. The primer/template is bound to a streptavidin-coated SPA bead. $^3$H-TTP is incorporated into the primer by reverse transcription. In brief, $^3$H-TTP, at a final concentration of 0.5 Ci/sample was diluted in RT assay buffer (49.5 mM Tris-HCl, pH 8.0, 80 mM KCl, 10 mM $MgCl_2$, 10 mM DTT, 2.5 mM EGTA, 0.05% Nonidet-P-40), and added to annealed DNA/RNA bound to SPA beads. The compound being tested was added to the reaction mixture at 0.001 µM–100 µM concentrations. Addition of 10 mU of recombinant RT and incubation at 37° C. for 1 hour resulted in the extension of the primer by incorporation of $^3$H-TTP. The reaction was stopped by addition of 0.2 ml of 120 mM EDTA. The samples were counted in an open window using a Beckman LS 7600 instrument (Beckman Instruments, Fullerton, Calif.).

Percent inhibition of virus replication was calculated by comparing the p24 antigen values or RT activity from the test drug-treated infected cells with p24 antigen values or RT activity from untreated infected cells. The anti-HIV activity of compounds was expressed as the $IC_{50}$ values, calculated from the dose-response curves, and defined as the drug concentration that decreases the HIV-1 RT activity or p24 antigen production in HIV-1 infected PBMCs, by 50%. In parallel, the effects of various treatments on cell viability were examined using a microculture tetrazolium assay (MTA), using 2,3-bis(2-methoxy-4-nitro-5-sulfophenyl)-5- [(phenylamino)-carbonyl]-2H-tetrazolium hydroxide (XTT), as disclosed in Uckun et al., ANTIMICROB AGENTS CHEMOTHER, 42:383–388 (1998).

. C. Assays of Sperm Immobilizing Activity (SLA)

To evaluate the spermicidal effects of trovirdine, D-PBT, F-PBT, S-DABO, and ZDV in comparison with N-9, highly motile fractions of pooled donor sperm (n=6) were prepared by discontinuous (90–45%) Percoll gradient (Conception Technologies, San Diego, Calif.) centrifugation and the "swim-up" method as described in D'Cruz et al., BIOL REPROD, 54:1217–1228 (1996). All donor sperm specimens were obtained after informed consent and in compliance with the guidelines of the Hughes Institute Institutional Review Board. Motile sperm ($\geq 10 \times 10^6$/ml), were suspended in 1 ml of Biggers, whitten, and Whittingam's medium (BWW) containing 25 mM HEPES (Irvine Scientific, Santa Ana, Calif.), and 0.3% BSA in the presence and absence of serial two-fold dilutions of test substance (500 µM to 31.2 µM) in 1% DMSO. The stock solutions of NNIs were prepared in DMSO (100 mM) and diluted in assay medium to yield the desired concentrations. Corresponding volume of DMSO (1%) was added to control tubes. N-9 was diluted in BWW-0.3% BSA (pH 7.4) to yield the desired concentrations (31.2 µM to 500 µM). After 3 hours of incubation at 37° C., the percentage of motile sperm was evaluated by CASA by procedures as described in D'Cruz et al., BIOL REPROD, 58:1515–1526, (1998); and D'Cruz et al., MOL HUM REPROD, 4:683–693 (1998). The percent motilities were compared with sham-treated control suspensions of motile sperm. The spermicidal activity of test compounds was expressed as the $EC_{50}$ (the final concentration of the compound in medium that decreases the proportion of motile sperm by 50%).

To test the effect of duration of incubation on SIA of spermicidal NNIs, motile fractions of sperm ($10^7$/ml) were incubated at 37° C. in BWW-0.3% BSA in the presence of 1 mM F-PBT, S-DABO in 1% DMSO or 1% DMSO alone as vehicle control. At timed intervals of 5 or 10 minutes, duplicate aliquots (4-µl) were transferred to two 20 µm Microcell chambers (Conception Technologies) and sperm motility was assessed by CASA for a duration of 60 minutes.

D. Sperm Kinematic Parameters

For CASA, 4 µl of each sperm suspension were loaded into two 20-µm Microcell chambers in a counting chamber at 37° C. At least 5–8 fields per chamber were scanned for analysis using a Hamilton Thome Integrated Visual Optical System (IVOS), version 10 instrument (Hamilton Thorne Research Inc., Danvers, Mass.). Each field was recorded for 30 seconds. The computer calibrations were set at 30 frames at a frame rate of 30/second. Other settings were as follows: minimum contrast 8; minimum size 6; low-size gate, 1.0; high-size gate, 2.9; low-intensity gate, 0.6; high-intensity gate, 1.4; phase-contrast illumination; low path velocity at 10 µm/s, and threshold straightness at 80%; and magnification factor, 1.95.

The sperm kinematics parameters that were determined included numbers of motile (MOT) and progressively (PRG) motile sperm; curvilinear velocity (VCL; a measure of the total distance traveled by a given sperm during the acquisition divided by the time elapsed); average path velocity (VAP; the spatially averaged path that eliminates the wobble of the sperm head), straight line velocity (VSL; the straight-line distance from beginning to end of track divided by time taken), beat cross frequency (BCF; frequency of sperm head crossing sperm average path), the amplitude of lateral head displacement (ALH; the mean width of sperm head oscillation), and the derivatives, straightness (STR=VSL/ VAP×100) and linearity (LIN=VSL/VCL×100; departure of sperm track from a straight line). Data from each individual cell track were recorded and analyzed. At least 200 motile sperm were analyzed for each aliquot sampled.

E. Confocal Laser Scanning Microscopy (CLSM)

The percentages of sperm with an intact acrosome following a 6 hour treatment with and without increasing concentrations (31.2 µM to 500 µM) of the three NNIs (S-DABO, F-PBT and D-PBT in comparison to N-9 were evaluated by CLSM. Ethanol permeabilized and airdried sperm smears were stained sequentially with the three fluorescent markers, FITC-*Pisum sativum* lectin, TOTO-3 iodide, and Nile red (Molecular Probes, Eugene, Oreg.) because their targets are different (acrosome, nucleus, and membrane lipid respectively). Samples were examined under a BioRad MRC-1024 Laser Scanning Confocal Microscope (BioRad Laboratories, Hercules, Calif.) equipped with a krypton/argon mixed gas laser (excitation lines 488, 568, and 647 nm) and mounted on a Nikon Eclipse E800 series upright microscope. The fluorescence emission of fluorescein, TOTO-3 iodide, and Nile red from the acrosomal region, nucleus, and the plasma membrane of sperm after ethanol permteabilization were simultaneously detected using the 598/40 nm, 522 DF32, and 680 DF32 emission/filter, respectively. Confocal images were obtained using a Nikon 100×(NA 1.35) objective lens and Kalman collection filter. Digitized images were saved on a Jaz disk (Iomega Corporation, Roy, UT) and processed using Lasersharp Bio-Rad) with the Adobe Photoshop software (Adobe Systems, Mountain View, Calif.). Final images were printed on a Fuji Pictrography 3000 (Fuji Photo Film Co., Tokyo, Japan) color printer.

F. Cell Proliferation Assay

Normal human ectocervical (CrEC 4627) and endocervical epithelial cells (CrEC-En 4312) were obtained from Clonetics, (San Diego, Calif.) and propagated in T-150 cm$^2$ tissue culture flasks (Corning Corp., Corning, N.Y.) in small airway epithelial cell basal medium (Clonetics) supplemented with 50 µg/ml BPE, 0.5 µg/ml hydrocortisone, 0.5 µg/ml hEGF, 0.1 µg/ml retinoic acid, 10 µml trasferrin, 5 µg/ml insulin, 5 µg/ml epinephrine, and 0.5 mg/ml BSA-FAF. To determine the growth-inhibitory effects of F-PBT and S-DABO in comparison with N-9, we used a MTT (3-[4,5-dimethyl thiazol-2-yl]-2,5-diphenyltetrazolium bromide)-based colorimetric assay for quantitation of cell proliferation as described in Narla et al., CLIN CANCER RES, 4:1405–1414 (1998).

Briefly, cells were harvested with 0.125% (w/v) trypsin-0.02% EDTA (GIBCO) from exponential-phase maintenance cultures and centrifuged (300 g×5 minutes). After suspension and counting, cells were dispensed within triplicate 96-well tissue culture plates in 100 µl volumes. After 3 and 24 hour incubation, the culture medium was discarded and replaced with 100 µl of fresh medium containing serial two-fold dilutions of drugs in medium to yield 3.9 µM to 250 µM for N-9 and 250 µM to 4 mM for F-PBT and S-DABO. NNIs were reconstituted in DMSO to a concentration of 100 mM. Stock solution of N-9 wasmade in sterile PBS. Control wells with medium containing 0.25% of DMSO alone were included as controls. Culture plates were then incubated for 24 hour before adding 10 µl of MTT solution (5 mg/ml in PBS) to each well. Wells containing only medium and MTT were used as control for each plate. The tetrazolium/formazan reaction was allowed to proceed for 4 hours at 37° C., and then 100 µl of the solubilization buffer (10% sodium dodecyl sulfate in 0.1% HCl) was added to all wells and mixed thoroughly to dissolve the dark blue formazan crystals.

After an overnight incubation at 37° C., the optical densities (OD) at 540 nm were measured using a 96-well multiscanner autoreader with the solubilization buffer serving as blank, To translate the $OD_{540}$ values into the number of live cells in each well, the $OD_{540}$ values were compared to those on standard $OD_{540}$-versus-cell number curves generated for each cell line. The percent survival was calculated using the formula: % survival=Live cell number [test]/Live cell number [control]×100. All assays were run in triplicate and the results were expressed as $IC_{50}$ values. The $IC_{50}$ was defined as the concentration required for 50% reduction in cell survival.

G. Statistical Analysis

Results are presented as the mean or mean±SD values from independent measurements. The statistical significance of difference between test groups was analyzed by one-way analysis of vairance and Dunnett's multiple comaparison test. Linear regression analysis was used to find correlated values between two measured parameters. A p value of <0.05 was considered significant. Non-linear regression analysis were used to find $IC_{50}$ and $EC_{50}$ values from the concentration effect curves using the GraphPad PRISM version 2.0 software program (San Diego, Calif.).

II. RESULTS

A. Tables

The following two tables will be referred to in discussing the results of the experiments:

TABLE 1

Effect of three novel NNIs on the enzymatic activity of purified recombinant HIV-RT, p24 antigen production in HIV-infected PBMC, and human sperm motility.

| | Anti-HIV activity | | |
|---|---|---|---|
| Compound | rRT[a] $IC_{50}$ rRT(µM)[b] | $HTLV_{IIIB}$ $IC_{50}$p24 (µM)[c] | Spermicidal activity $EC_{50}$ (µM)[d] |
| D-PBT | 0.1 | <0.001 | >500 |
| F-PBT | 0.4 | <0.001 | 147 |
| S-DABO | 6.1 | <0.001 | 202 |
| Trovirdine | 0.8 | 0.007 | >500 |
| N-9 | Nd[e] | 2.2 | 81 |

[a]Recombinant HIV reverse transcriptase.
[b]$IC_{50}$ RT = Drug concentration inhibiting HIV-RT activity by 50%.
[c]$IC_{50}$ p24 = Drug concentration inhibiting HIV-p24 antigen production by 50%.
[d]$EC_{50}$ Drug concentration inhibiting sperm motility by 50%.
[e]ND = not determined.

TABLE 2

Effect of F-PBT and N-9 on cell growth of normal human ectocervical and endocervical epithelial cells as quantitated by MTT assay.

| | Sperm | Ectocervical epithelial cells[a] | | Endocervical epithelial cells[a] | |
|---|---|---|---|---|---|
| Treatment | $EC_{50}$ (µM)[b] | $IC_{50}$ (µM)[c] | SI[d] | $IC_{50}$ (µM) | SI |
| F-PBT | 147 | >1000 | >6.8 | >1000 | >6.8 |
| S-DABO | 202 | >4000 | >19.8 | >4000 | >19.8 |
| N-9 | 81 | 15 | 0.18 | 11 | 0.13 |

[a]Cell proliferation was tested after 24 hours treatment with 5 different concentrations (250 µM to 4000 µM) of F-PBT and S-DABO.
[b]$EC_{50}$ = Drug concentration inhibiting sperm motility by 50%.
[c]$IC_{50}$ = Drug concentration inhibiting cell growth by 50%.
[d]SI = Selectivity Index is equal to the ratio of $IC_{50}$ to $EC_{50}$.

B. Anti-HIV Activity of Novel NNIs

The effect of the three novel NNI derivatives shown in FIG. 1 as well as trovirdine were tested for RT inhibitory activity in cell-free assays using purified recombinant HIV RT (listed as $IC_{50}$[rRT], and by in vitro assays of anti-HIV activity in $HTLV_{IIIB}$-infected PBMCs ($IC_{50}$[p24]). As shown in Table 1, all three NNIs elicited potent anti-HIV activity with an $IC_{50}$ values of less than 1 nM, as measured by p24 production in HIV-infected human PBMCs. Trovirdine, the most potent NNI reported to date, was at least 7-fold less potent under identical experimental conditions. Also, D-PBT and F-PBT were 2- to 8-fold more potent than trovirdine in inhibiting recombinant HIV RT. The observed reduction in RT activity and p24 production by the 3 NNIs were not due to any cytotoxic effects by these new agents since cell viability of PBMC was not affected even at the highest concentrations tested ($IC_{50}$[MTA]>100 $\mu$M). The anti-HIV activity ($IC_{50}$[p24]) of the three novel NNIs was at least 2000-fold more potent than that of the detergent-type microbicide, N-9 ($IC_{50}$=2.2 $\mu$M).

C. Spermicidal Activity of Novel NNIs

Figure 2:
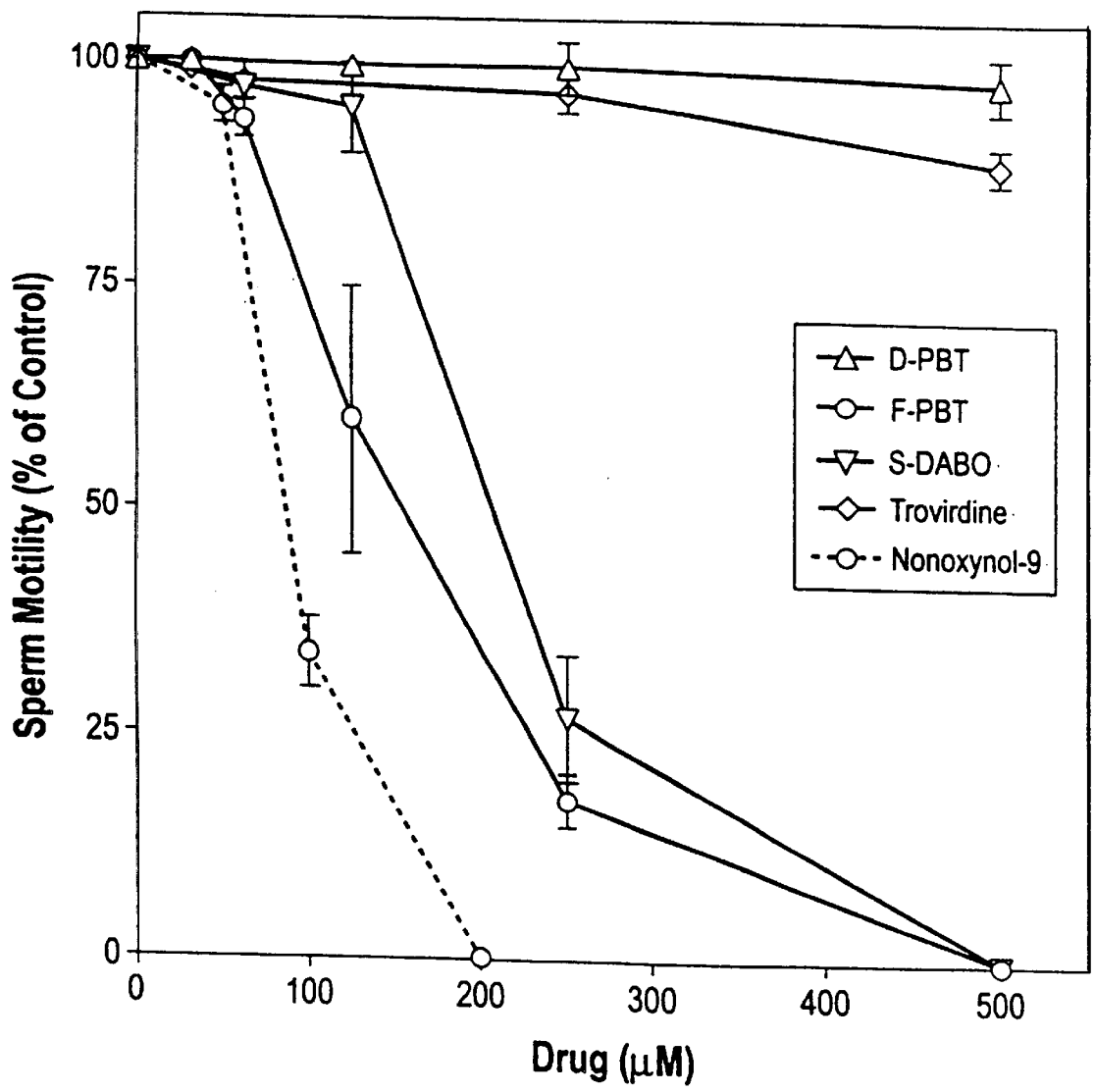
FIG. 2 is a graph showing concentration-dependent inhibition of sperm motility by trovirdine, D-PBT, F-PBT, S-DABO, and N-9. Highly motile fraction of sperm were incubated for 3 hours with increasing concentrations (31.2 $\mu$M–500 $\mu$M) of trovirdine, D-PBT, F-PBT, S-DABO, and N-9 or 1% DMSO in the assay medium, and the percentage of motile sperm were evaluated by CASA. Each data point represents the mean from three to four independent experiments.
Figure 3:
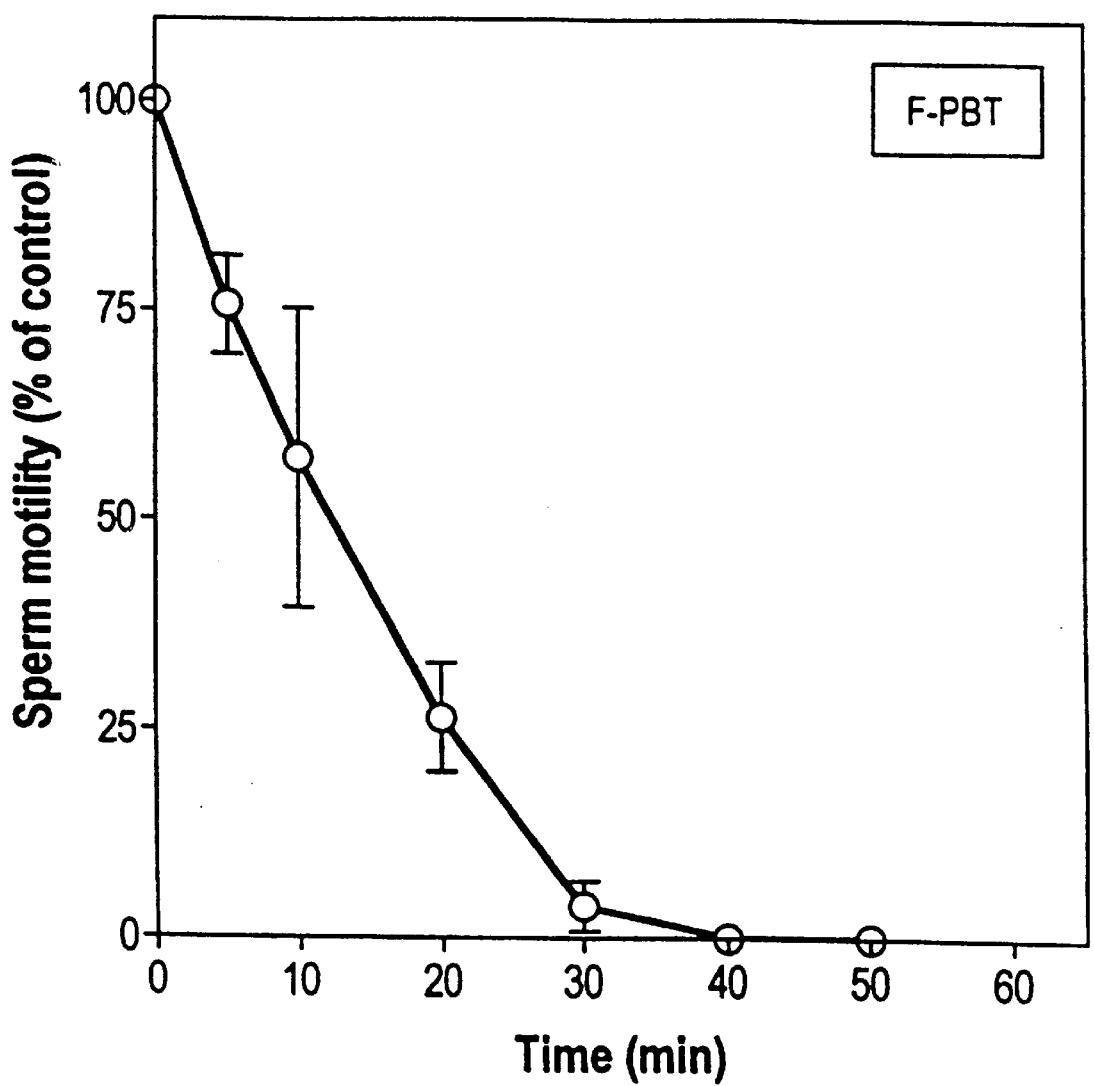
FIG. 3 is a graph showing time-dependent sperm immobilization in the presence of F-PBT. Motile sperm were incubated at 37° C. in assay medium in the presence of 1 mM F-PBT or 1% DMSO alone. At timed intervals of 5 or 10 minutes, sperm motility was assessed by CASA. Each data point represents the mean±SD from two independent experiments.

Next, the effects of the three NNIs (S-DABO, D-PBT, and F-PBT) and trovirdine on human sperm function were examined in comparison to N-9. Exposure of the highly motile fraction of human sperm to trovirdine or D-PBT did not affect sperm motility even at concentrations as high as 500 $\mu$M (see FIG. 2 and Table 1). Further, sperm motion kinematics using CASA confimed that trovirdine or D-PBT treatment did not alter the sperm motion parameters, such as the progressive motility (PRG), track speed (VCL), path velocity (VAP), straight line velocity (VLS), straightness of the swimming pattern (STR), linearity of the sperm tracks (LIN), beat-cross frequency (BCF), and the amplitude of lateral sperm-head displacement (ALH). In contrast to trovirdine or D-PBT, introduction of a fluorine atom at the ortho position of phenyl ring in PBT or an isopropyl group at the C-5 position of the thymine ring of S-DABO resulted in a concentration-dependent spermicidal activity. The $EC_{50}$ value of 147 $\mu$M (95% CI: 94–330 $\mu$M) obtained for F-PBT was within the spermicidal range of N-9 ($EC_{50}$ value 81 $\mu$M; 95% CI: 41–410 $\mu$M) (see FIG. 2 and Table 1). Also, the evaluation of the kinetics of sperm immobilization by CASA showed a linear relationship between incubation time and loss of progressive sperm motility after exposure to compound F-PBT (correlation coefficient 0.811, p>0.005) (see FIG. 3). The time required for 50% motility loss of progressively motile sperm exposed to F-PBT was 10 minutes (95% CI: 8–12 minutes). By comparison, the sperm motility in control samples remained stable (95%±3% compared to baseline) during the 60 minutes monitoring period.

Figure 4:
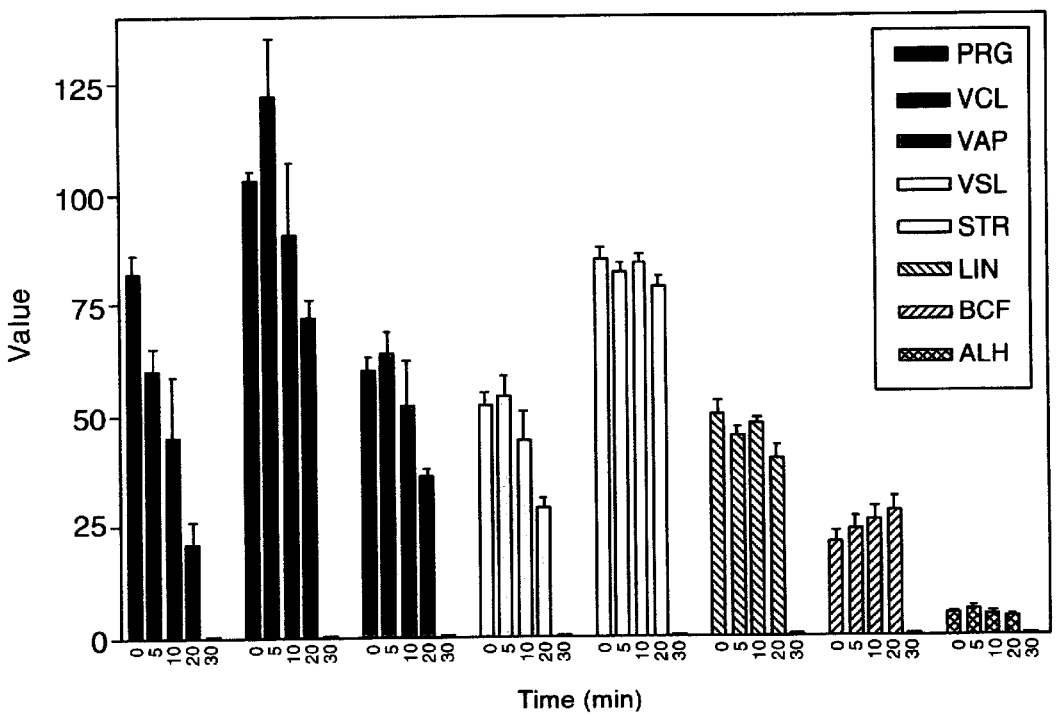
FIG. 4 is a graph showing the effect of F-PBT on sperm motion parameters. Motile fractions of sperm were incubated in assay medium in the presence of 1 mM F-PBT and the time-dependent motility characteristics were determined using the Hamilton Thome-IVOS version 10 CASA as described under "Materials and Methods." Values: $\mu$m/s for VCL, VAP, VSL; $\mu$m for ALH; % for MOT, STR, LIN, and Hz for BCF.

The time-dependent sperm motility loss (PRG) induced by F-PBT was associated with significant changes in the movement characteristics of the surviving sperm particularly with respect to the track speed (VCL), path velocity (VAP), and straight line velocity (VSL). The representative sperm kinematic parameters of F-PBT-treated sperm versus time is shown in FIG. 4. The decreases in VSL and VCL or VSL and VAP were similar in magnitude. Therefore, values for linearity (LIN) of the sperm tracks and the straightness (STR) of the swimming pattern remained relatively constant. Also, the beat cross frequency (BCF), and the amplitude of lateral sperm-head displacement (ALH) were relatively stable as the proportion of motile sperm declined during the linear phase of motility loss. The sperm motion parameters of control sperm showed no significant changes during the 60 minutes incubation period.

D. Spermicidal NNIs Lack Detergent-Like Membrane Toxicity

Nonoxynol-9, the most widely used vaginal spermicide, immobilizes sperm as a result of a detergent-type action on the sperm plasma membrane. Because of its membrane disruptive properties, continued use of N-9 has been shown to damage the cervicovaginal epithelium, cause an acute tissue inflammatory response, and enhance the likelihood of HIV infection by heterosexual tnansmission. A spermicide that does not elicit any non-specific membrane toxicity characteristic of detergent-type contraceptives would offer clinical advantages.

Figure 5A:
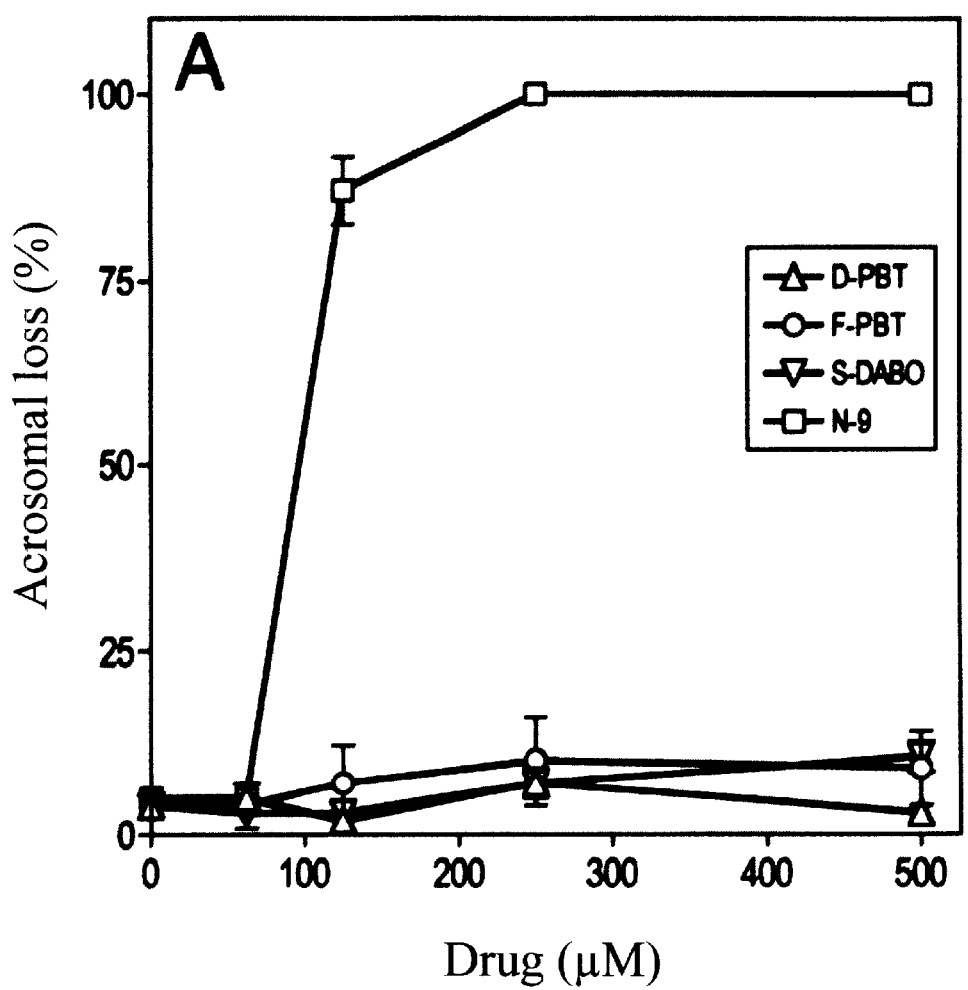
FIG. 5A is a graph showing the effect of D-PBT, F-PBT, S-DABO, and N-9 on sperm acrosomal membrane integrity. Motile sperm were preincubated in the presence or absence of increasing concentrations of the three NNIs and N-9 for 6 hours. The percentage of acrosome-intact sperm determined by FITC-*Pisum sativum* lectin binding assay were expressed as the mean±SD of three separate experiments.
Figure 5B:
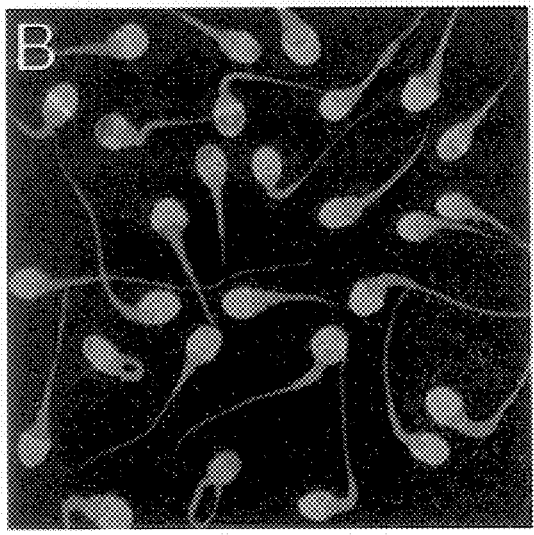
FIGS. 5B through 5E are laser scanning confocal fluorescence images of sperm. The sperm shown are triple labeled with FITC-*Pisum sativum* lectin for acrosome (green), TOTO-3 iodide for DNA (blue), and Nile red for membrane lipid (red). In acrosome-intact sperm, the acrosomal region of the sperm heads exhibited a uniform, bright green fluorescence. In acrosome-reacted sperm, green fluorescence was either absent or restricted to the equatorial segment of the sperm heads.
Figure 5C:
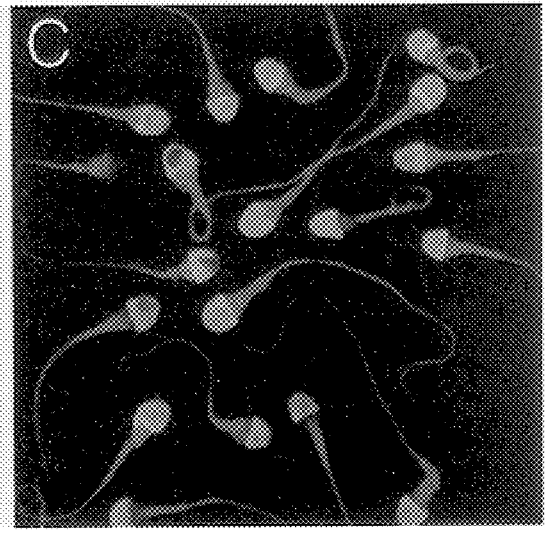
Figure 5D:
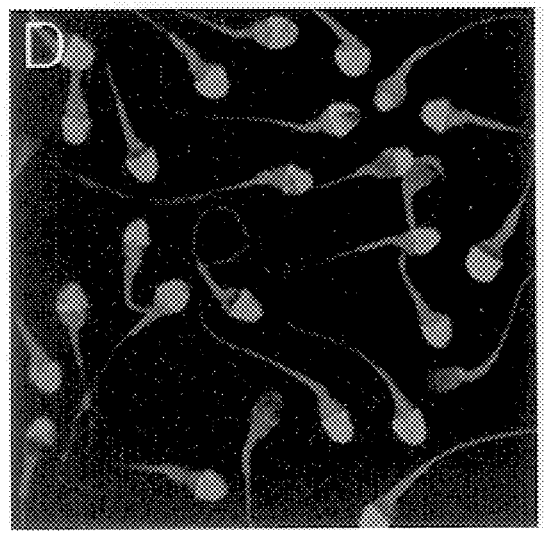
Figure 5E:
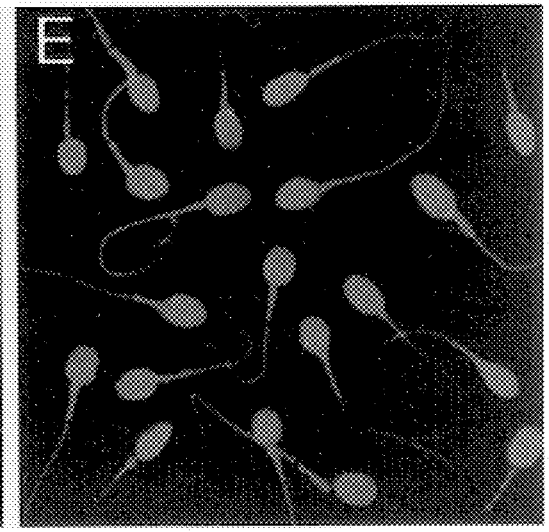

Therefore, the effects of F-PBT and S-DABO on sperm head acrosomal membrane integrity was tested as a marker for membrane damage by triple staining (FITC-*Pisum sativum* lectin for acrosome, TOTO-3 iodide for nuclear DNA, and Nile red for membrane lipids) of sperm using CLSM. Examination of FITC-lectin, TOTO-3, and Nile red-stained sperm by CLSM revealed an intense acrosomal staining with FITC-lectin (green), nuclear staining with TOTO-3 (blue), and membrane staining (red) with Nile red, respectively (see FIG. 5). By confocal microscopy, despite complete immobilization of sperm in the presence of F-PBT and S-DABO, >90% of the treated sperm revealed acrosomal staining after 6 hours of incubation when compared with N-9 which revealed complete loss of acrosomal staining (see FIG. 5A). Thus, the spermicidal activity of compound F-PBT was not caused or accompanied by membrane disruption. In sperm exposed to vehicle (i.e., 1% DMSO) alone (shown in FIG. 5B) or 500 $\mu$M F-PBT (shown in FIG. 5C) or S-DABO (shown in FIG. 5D) for 6 hours more than half of the sperm head (i.e., the acrosomal region) exhibited a uniform, bright green fluorescence, indicating that the acrosomes remained intact. By comparison, sperm exposed to 500 $\mu$M of N-9 (shown in FIG. 5E) under identical conditions, showed no green fluorescence due to disruption of membrane integrity and loss of acrosomal membranes. These properties of F-PBT and S-DABO are in sharp contrast to the activity profile of the currently used spermicide, N-9, which exerts its effects via a detergent-like ability to damage the sperm membranes thereby impairing the sperm function.

E. Selective Spermicidal Activity of F-PBT and S-DABO versus N-9

The MTT assay measuring the cell proliferation and viability was used to test the in vitro cytotoxicity of F-PBT and S-DABO in comparison to N-9 against confluent monolayers of normal human ectocervical and endocervical epithelial cells. Cells were exposed to these compounds at doses ranging from 3.9 $\mu$M to 4 mM for 3 hours or 24 hours. The concentration-response cell survival curves for F-PBT and S-DABO versus N-9 for these cells measured by the MTT assay were compared with spermicidal activity measured by CASA. In MTT assays, N-9 exhibited significant cytotoxicity to ectocervical epithelial and endocervical epithelial cells with mean $IC_{50}$ values of 15 $\mu$M and 11 $\mu$M, respectively. By comparison, the $IC_{50}$ values for F-PBT and S-DABO dose survival curves for ectocervical and endocervical epithelial cells were >4 mM for S-DABO and >1 mM for F-PBT respectively (see Table 2). Thus, N-9 was spermicidal only at cytotoxic concentrations ($EC_{50}$ value: 81 $\mu$M; selectivity indices: 0.18 and 0.13 for ectocervical and endocervical cells respectively), whereas, F-PBT and S-DABO showed high selectivity indices against these cells (SI: >6.8 and >19.8 for ectocervical cells and endocervical cells respectively). Thus, F-PBT and S-DABO were significantly less active against these reproductive tract cells. These studies demonstrate that the spermicidal activity of F-PBT and S-DABO was not related to non-specific cytotoxicity.

III. DISCUSSION OF RESULTS OF EXPERIMENT

A. Anti-HIV Activity

Previous modeling studies have revealed several potential ligand derivatization sites for the generation of more potent NNIs. Modifications of PETT derivative, trovirdine, which was accomplished by replacing the pyridyl ring with a 2,5-dimethoxyphenyl group, D-PBT (N-[2-(2,5-dimethoxyphenethyl)]-N'-[2-(5-bromopyridyl)]thiourea) or fluorine atom at the ortho position, F-PBT (N-[2-[2-(2-fluorophenethyl)]-N'-[2-(5-bromopyridyl)]-thiourea), of the phenyl ring led to more potent anti-HIV drugs. Biological assays confirmed that these two NNIs were more active (at least 7-fold) than trovirdine, one of the most potent PETT derivatives reported to date, with anti-HIV activity with $IC_{50}[p24]$ values of less than 1 nM. Computer docking procedures also showed that the addition of a isopropyl group at the 5th position of the thymine ring of S-DABO would lead to higher affinity for the relatively hydrophobic environment at this location of the binding pocket of S-DABO. The DABO derivative, 5-isopropyl-2-[(methylthiomethyl)thio]-6-benzyl)-pyrimidin-4-(1H)-one (S-DABO) elicited potent anti-HIV activity with an $IC_{50}$ value less than 1 nM for inhibition of HIV replication. Thus, all three NNIs were >2000-fold more potent than N-9.

NNIs have been found to bind to a specific allosteric site of HIV-1 RT near the polymerase site and interfere with reverse transcription by altering either the conformation or mobility of RT, thereby leading to noncompetitive inhibition of the enzyme. A number of amino acid residues in contact with the NNIs are relatively flexible and vary from structure to structure and can be displaced by the right NNI. These residues include Tyr180, Tyr181, Tyr318, Try319, Phe227, Leu234, Trp229, Pro95, and Glu138 (from p51 subunit of RT). The enhanced anti-HIV activity of the novel PBT and DABO derivatives studied here is most likely due to their larger molecular surface favoring the binding pocket of NNI, as well as to greater lipophilicity (due to substitution of a bulkier dimethoxyphenyl group in place of phenyl ring), better hydrophobic contact (due to the substitution of isopropyl at the C-5 position of the thymine ring), and closer contact (due to substitution of methoxy groups at meta/ortho positions or fluoro group at the ortho position of the unsubstituted phenyl ring) with target amino acid residues, Pro95 and Trp229 of RT (44,45). In addition, this change in conformation in turn could affect the positions of neighboring amino acid residues particularly Tyr183 and Tyr188 which may contribute to the inactivation of HIV-1 RT. The docking studies indicated that the 2-methoxy group of D-PBT provides close contact with residues Pro195 and Trp229. This suggested that a combination of all the structural merits unique to each lead compound can yield more potent RT inhibitors.

B. Spermicidal Activity

Sperm motion kinematics combined with confocal laser scanning microscopy demonstrated that F-PBT and S-DABO caused cessation of sperm motility in a concentration and time dependent fashion without, unlike the detergent spermicide, N-9, affecting the sperm plasma and acrosomal membrane integrity. Furthermore, F-PBT and S-DABO were selectively spermicidal when compared with N-9 which was cytotoxic to human ectocervical as well as endocervical epithelial cells at spermicidal doses. Thus, the ectocervical epithelial cells appear to be vulnerable to cytotoxic insults from the detergent-type spermicide, N-9. The gain of spermicidal functions of the novel NNIs of the invention suggest that further modifications of these NNIs could lead to even more potent dual-ftmction NNIs with dual-function anti-HIV and spermicidal activities as well as reduced cytotoxicities to genital tract epithelial cells.

The synthesis of novel NNIs as dual-function anti-HIV agents with potent spermicidal activity represents a significant step forward in the development of new microbicides for curbing heterosexual vaginal HIV transmission. These promising results illustrate that dual-finction NNIs shows unique clinical potential to become the active ingredient of a new female-controlled topical virucidal vaginal contraceptive for women who are at high risk for acquiring HIV by heterosexual vaginal transmission.

The invention described herein may be modified to include alternative embodiments. All such obvious alternatives are within the spirit and scope of the invention, as claimed below.

Throughout this application various publications are referenced. The disclosures of these publications in their entireties are hereby incorporated by reference into this application in order to more fully describe the state of the art to which this invention pertains.

We claim:

1. A method of inhibiting conception in a mammal, the method comprising contacting mammalian sperm with an effective spermicidal amount of the compound comprising the formula:

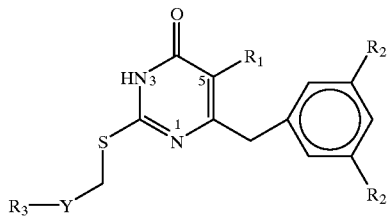

where $R_1$ and $R_2$ are alike or different, and are hydrogen, halo, alkyl, alkenyl, hydroxy, alkoxy, thioalkyl, thiol, phosphino, ROH, or RNH group, where R is alkyl;

Y is S or O; and $R_3$ is alkyl, alkenyl, aryl, aralkyl, ROH, or $RNH_2$ group, where R is alkyl;

or a pumiarcutically acceptable salt thereof.

2. The method of claim 1, wherein the compound is selected from the group consisting of:

5-methyl-2-[(methylthiomethyl)thio]-6-benzyl-pyrimidin-4-1H-one;

5-ethyl-2-[(methylthiomethyl)thio]-6-benzyl-pyrimidin-4-1H-one;

5-isopropyl-2-[(methylthiomethyl)thio]-6-benzyl-pyrimidin-4-1H-one;

5-isopropyl-2-[(methylthiomethyl)thio]-6-(3,5-dimethylbenzyl)-pyrimidin-4-1H-one; and pharmaceutically acceptable salts thereof.

3. The method of claim 2, wherein the compound is selected from 5-isopropyl-2-[(methylthiomethyl)thio]-6-(benzyl)-pynmidin-4-(1H)-one; and pharmaceutically acceptable salts thereof.

4. A method for inhibiting the motility of sperm, tho method comprising contacting sperm with a sperm mobility inhibiting effective amount of the compound comprising the formula:

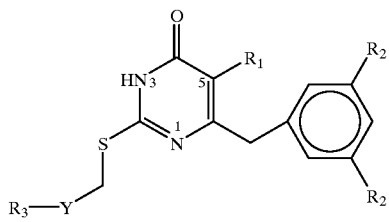

where $R_1$ and $R_2$ are alike or different, and are hydrogen, halo, alkyl, alkenyl, hydroxy, alkoxy, thioalkyl, thiol, phosphino, ROH, or RNH group, where R is alkyl;

Y is S or O; and $R_3$ is alkyl, alkenyl, aryl, arkl, ROH, or $RNH_2$ group, where R is alkyl;

or a pharmaceutically acceptable salt thereof.

5. The method of claim 4, wherein the compound is selected from the group consisting of:

5-methyl-2-[(methylthiomethyl)thio]-6-benzyl-pyrimidin-4-1H-one;

5-ethyl-2-[(methylthiomethyl)thio]-6-benzyl-pyrimidin-4-1H-one;

5-isopropyl-2-[(methylthiomethyl)thio]-6-benzyl-pyrimidin-4-1H-one;

5-isopropyl-2-[(methylthiomethyl)thio]-6-(3,5-dimethylbenzyl)-pyrimidin-4-1H-one; and pharmaceutically acceptable salts thereof.

6. The method of claim 5, wherein the compound is selected from 5-isopropyl-2-[(methylthiomethyl)thio]-6-(benzyl)-pyrimidin-4-(1H)-one; and pharmaceutically acceptable salts thereof.

7. A composition comprising:

an effective spermicidal amount of the compound comprising the formula:

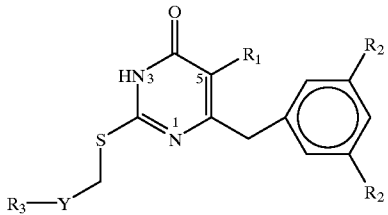

where $R_1$ and $R_2$ are alike or different, and are hydrogen, halo, alkyl, alkenyl, hydroxy, alkoxy, thioalkyl, thiol, phosphino, ROH, or RNH group, where R is alkyl;

Y is S or O; and $R_3$ is alkyl, alkenyl, aryl, aralky, ROH, or $RNH_2$ group, where R is alkyl;

or a pharnaceutically acceptable salt thereof; and a pharmaceutically acceptable carrier, diluent, or vehicle.

8. The composition of claim 7, wherein the compound is selected from the group consisting of:

5-methyl-2-[(methylthiomethyl)thio]-6-benzyl-pyrimidin-4-1H-one;

5-ethyl-2-[(methylthiomethyl)thio]-6-benzyl-pyrimidin-4-1H-one;

5-isopropyl-2-[(methylthiomethyl)thio]-6-benzyl-pyrimidin-4-1H-one;

5-isopropyl-2-[(methylthiomethyl)thio]-6-(3,5-dimethylbenzyl)-pyrimidin-4-1H-one; and pharmaceutically acceptable salts thereof.

9. The composition of claim 8, wherein the compound is selected from 5-isopropyl-2-[(methylthiomethyl)thio]-6-(benzyl)-pyrimidin-4-(1H)-one; and pharmaceutically acceptable salts thereof.

10. The composition of claim 7, wherein the pharmaceutical carrier provides both rapid and prolonged release of the spermicidal agent.

* * * * *